US007105160B1

(12) United States Patent
Smith

(10) Patent No.: US 7,105,160 B1
(45) Date of Patent: Sep. 12, 2006

(54) ANTIBODY-SERUM PROTEIN HYBRIDS

(75) Inventor: Bryan John Smith, Maidenhead (GB)

(73) Assignee: Celltech Therapeutics Limited, Berkshire (GB)

( * ) Notice: Subject to any disclaimer, the term of this patent is extended or adjusted under 35 U.S.C. 154(b) by 0 days.

(21) Appl. No.: 09/831,534

(22) PCT Filed: Nov. 10, 1999

(86) PCT No.: PCT/GB99/03747

§ 371 (c)(1),
(2), (4) Date: Jun. 16, 2001

(87) PCT Pub. No.: WO00/27435

PCT Pub. Date: May 18, 2000

(30) Foreign Application Priority Data

Nov. 10, 1998 (GB) ................. 9824632.5

(51) Int. Cl.
A61K 39/395 (2006.01)
A61K 38/38 (2006.01)
C07K 16/00 (2006.01)
C07K 16/46 (2006.01)
A61K 49/16 (2006.01)
A61K 51/00 (2006.01)

(52) U.S. Cl. .................. 424/179.1; 530/345; 530/362; 530/363; 530/391.1; 530/391.3; 530/391.5; 530/391.7

(58) Field of Classification Search ............. 530/391.1, 530/391.5, 345, 362; 424/179.1
See application file for complete search history.

(56) References Cited

U.S. PATENT DOCUMENTS 4,749,570 A * 6/1988 Poznansky
4,751,286 A * 6/1988 Packard et al.
5,670,132 A * 9/1997 Griffiths et al. ............ 424/1.11
5,714,142 A * 2/1998 Blaney et al. ............. 424/85.2
6,350,431 B1 * 2/2002 Snow et al.

FOREIGN PATENT DOCUMENTS

| WO | WO 92/22583 | 12/1992 |
| WO | WO 93/15199 | 8/1993 |
| WO | WO 97/34631 | 9/1997 |
| WO | WO 98/00171 A2 * | 1/1998 |

OTHER PUBLICATIONS

Delgado et al. British J. Cancer 73: 175-182, 1996.*
K.A. Barr, Pharmaceutical Engineering, Protocol for Efficient Secretion of HSA Developed from *Pichia pastoris*, 12:48-51, Mar./Apr. 1992.
L. Bartalena, Clinics in Laboratory Medicine, Thyroid Hormone Transport Proteins, 13:583-598, Sep. 1993.
M. Better, International Genetic Engineering, Inc., *Escherichia coli* Secretion of an Active Chimeric Antibody Fragment, 240:1041-043, May 1988.
F. Bree, Clinical Pharmacokinetics, Pharmacokinetcs of Intravenously Administered 125I-Labelled Human α1-Acid Glycoprotein, 11:336-342, 1986.
A.P. Chapman, Nature Biotechnology, therapeutic antibody fragments with prolonged in vivo half-lives, 17:780-783, Aug. 1999.
D.J. Chiswell, Tibtech, Phage antibodies: will new 'coliclonal' antibodies replace monoclonal antibodies?, 10:80-84, Mar. 1992.
J.M. Cregg, Bio/Technology, Recent advances in the Expression of foreign Genes in *Pichia pastoris*, 11:905-910, Aug. 1993.
R. Fleer, Bio/Technology, Stable Multicopy Vectors For High-Level Secretion of Recombinant Human Serum Albumin by Kluyveromyces Yeasts, 9:968-975, Oct. 1991.
D. Gitlin, Journal of Clinical Investigation, The Selectivity of the Human Placenta in the Transfer of Plasma Proteins from Mother to Fetus, 10:1938-1951, 1964.
A.H. Horwitz, Proceedings of the National Academy of Sciences of the United States of America, Secretion of Functional Antibody and Fab Fragment from Yeast Cells, 85:8678-8682, 1988.
D.R. Hurwitz, Transgenic Research, Specific combinations of human serum albumin introns direct high level expression of albumin in transfected COS cells and in the milk of transgenic mice, 3:365-375, 1994.
J.K. Kim, Eur. J. Immunol, Localization of the site of the murine IgG1 molecule that is involved in binding to the murin intestinal Fc receptor, 24:2429-2434, 1994.
W. Kramer, Nucleic Acids Research, The gapped duplex DNA approach to oligonucleotide-directed mutation construction, 12:9441-9457, 1984.
D. Kraus, Behring Inst. Mitt, Determination of Affinities of Murine and Chimeric Anti-χ/β- T Cell Receptor antibodies by Flow Cytomertry, 87:56-67, 1990.
C. Medesan, The American Association of Immunologists, Delineation of the Amino Acid Residues Involved in Transcytosis and Catabolism of Mouse IgG1$_1$, 158:2211-2217, 1997.
M. Nose, Proceedings of the National Academy of Sciences of the United States of America, 80:6632-6636, 1983, Biolog. Sign. of Carbohydrate Chains on Monoclonal Antibodies.
A. A. Ogunjimi, Biotechnology, High-level secretory expression of immunologically active intact antibody from the yeast *Pichia pastoris*, 21:561-567, 1999.

(Continued)

Primary Examiner—Christina Chan
Assistant Examiner—Marianne DiBrino
(74) Attorney, Agent, or Firm—Klauber & Jackson

(57) ABSTRACT

Hybrid proteins are described which comprise one or more antigen-binding antibody fragments covalently linked to one or more serum carrier proteins. The hybrid proteins can bind antigens, have a long half-life in vivo and can be used in medicine for therapy and diagnosis.

8 Claims, 9 Drawing Sheets

OTHER PUBLICATIONS

T. Peters, Advances in Protein Chemistry, Serum Albumin, 37:161-245, 1985.

F. Sanger, Proceedings of the National Academy of Sciences of the United States of America, 74:5463-5467, 1977.

D. Sleep, Bio/Technology, *Saccharomyces cerevisiae* Strains that Overexpress Heterologous Proteins, 9:183-187, Feb. 1991.

K. Sreekrishna, Gene, Strategies for optimal synthesis and secretion of heterologous protiens in the methylotrophic yeast *Pichia pastoris*, 190:55-62, 1997.

S. Syed, Blood, Potent Antithrombin Activity and Delayed Clearance from the Circulation Characterize Recombinant Hirudin Genetically Fused to Albumin, 89:3243-3252, May 1997.

M.H. Tao, Journal of Immunology, Studies of Aglycosylated Chimeric Mouse-Human IgG Role of Carbohydrate in the Structure and Effector functions Mediated by the Human IgG Constant Region, 143:2595-2601, Oct. 1989.

T.A. Waldmann, Progr. Allergy, Metabolism of Immunooglobulins, 13:1-110, 1969.

E.J. Wawrzynczak, Molecular Immunology, Blood Clearance in the Rat of a Recombinant Mouse Monoclonal Antibody Lacking the N-Linked Oligosaccharide Side Chains of the $C_H2$ Domains, 29:213-220, 1992.

N. Yukawa, Journal of Immunoassay, Bispecific Rabbit $Fab^9$-Bovine Serum Albumin Conjugate used in Hemagglutination Immunoassay for β-Microseminoprotein, 18:215-233, 1997.

P. Yeh, Proceedings of the National Academy of Sciences of the United States of America, Design of Yeast-Secreted Albumin Derivatives for Human Therapy: Biological and Antiviral Properties of a Serum albumin-CD4 Genetic Conjugate, 89;1904-1908, 1992.

\* cited by examiner

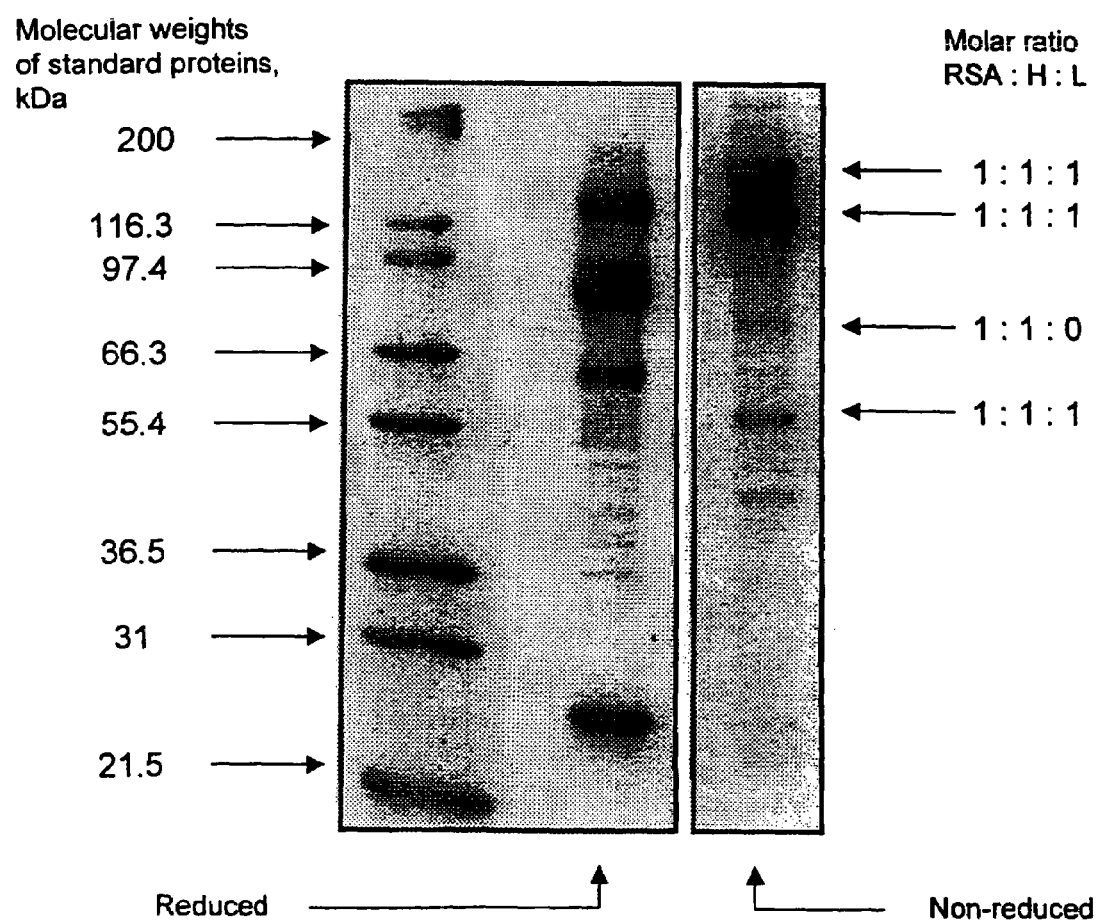
FIG. 1 SDS PAGE of RSA-FAB' conjugate

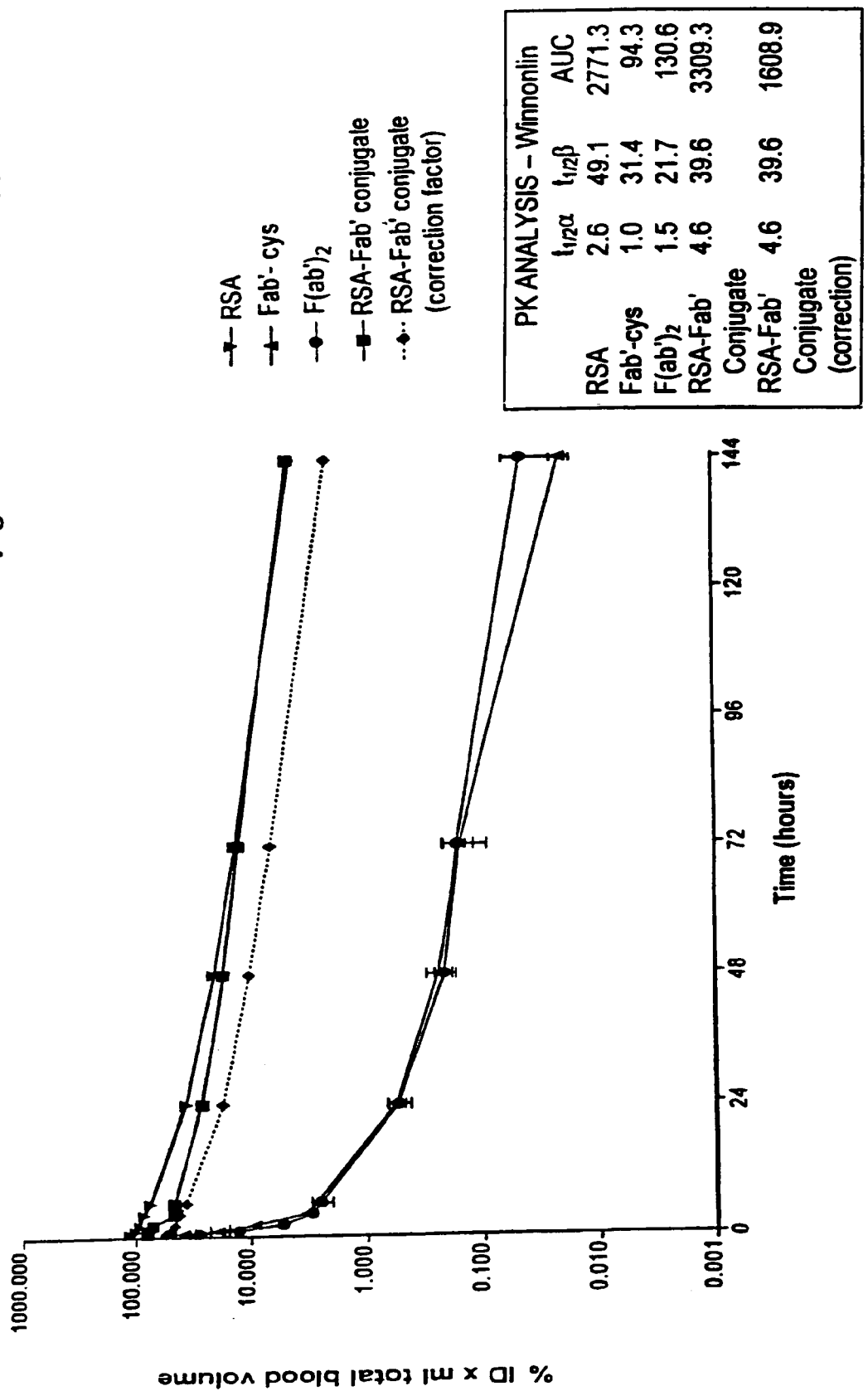

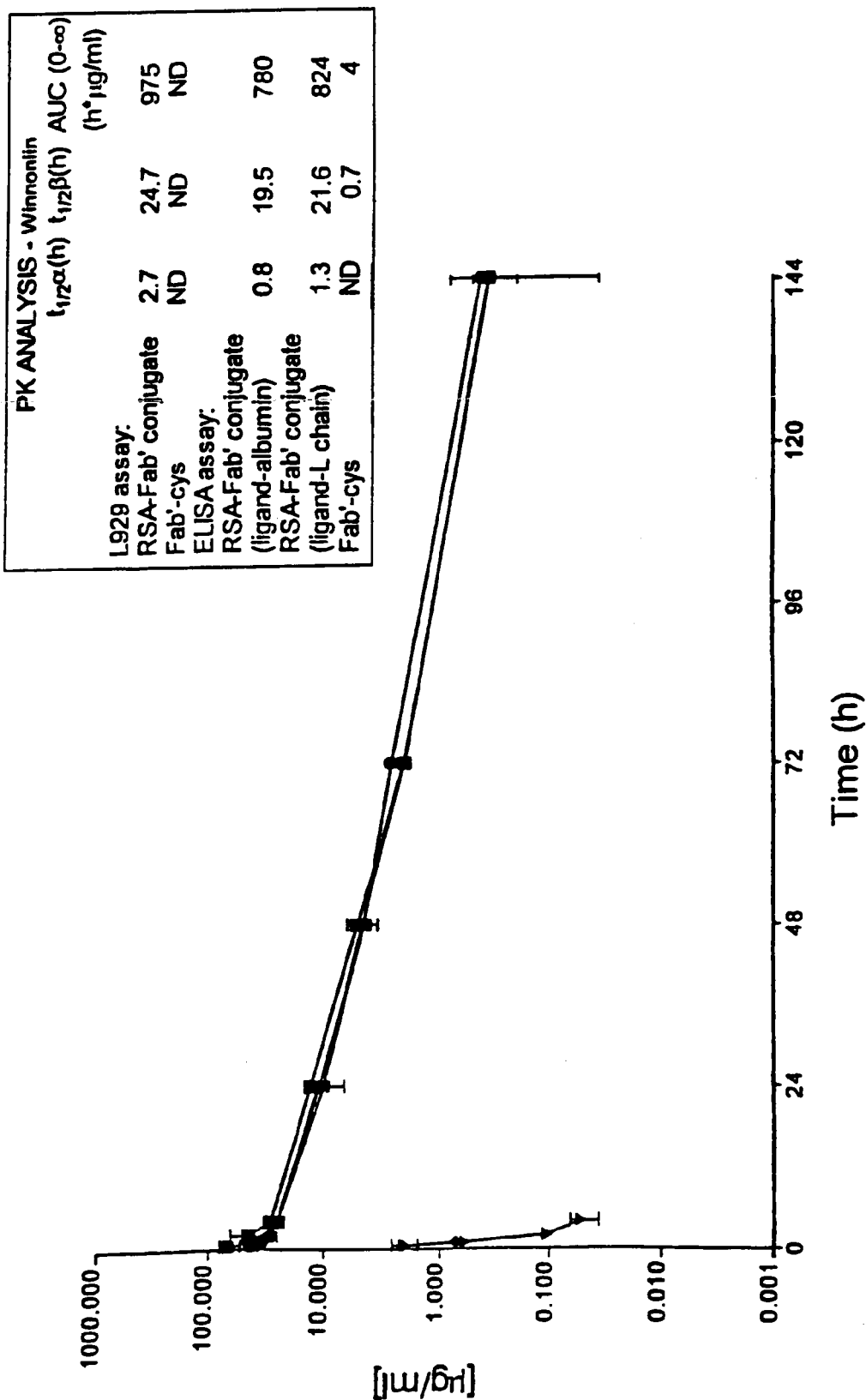
FIG. 3 Pharmacokinetics of RSA-Fab' or Fab'-cys in the rat (assayed by ELISA or cytokine neutralisation)

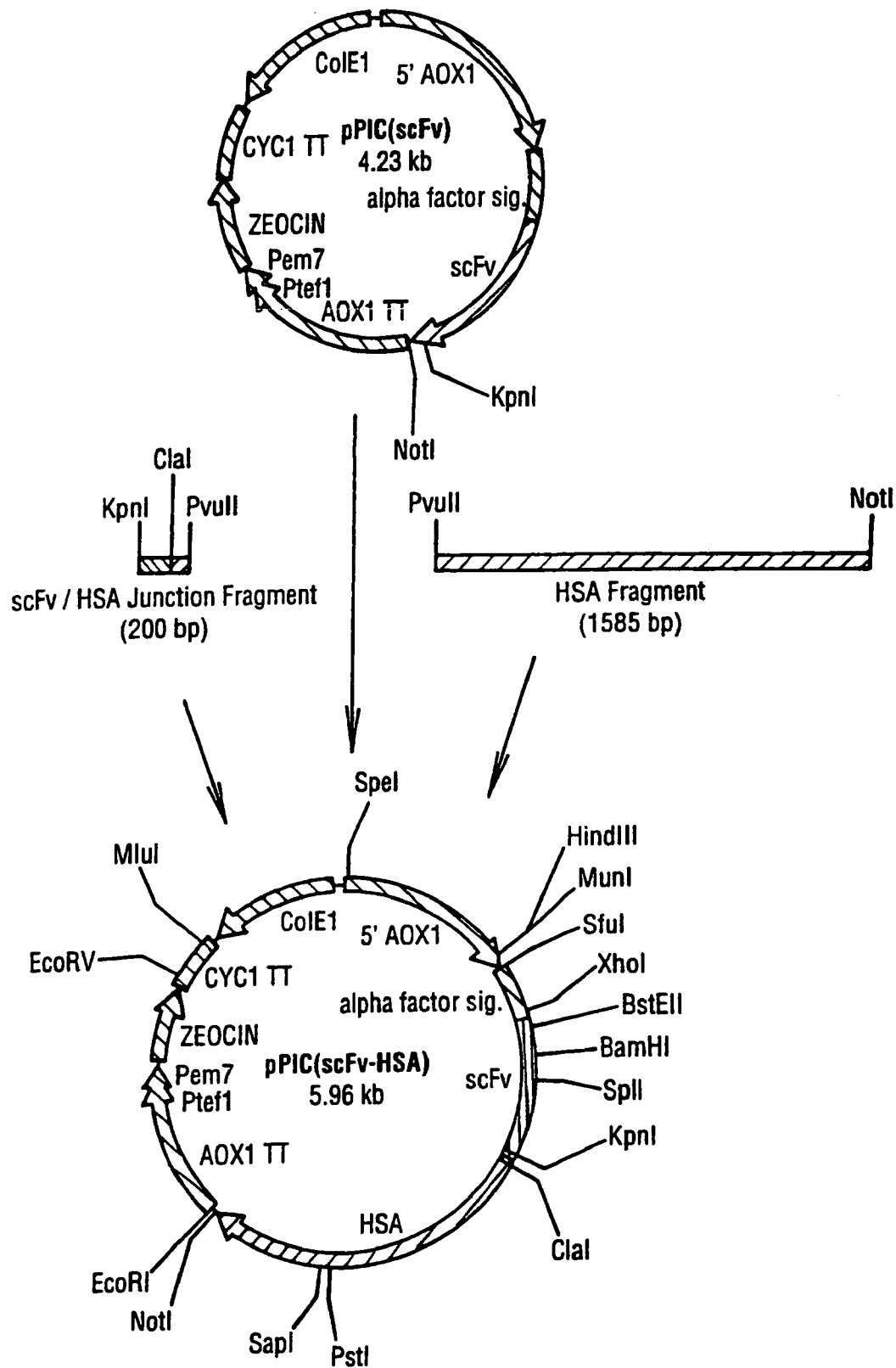
FIG. 4 Construction of pPIC (scFv-HSA)

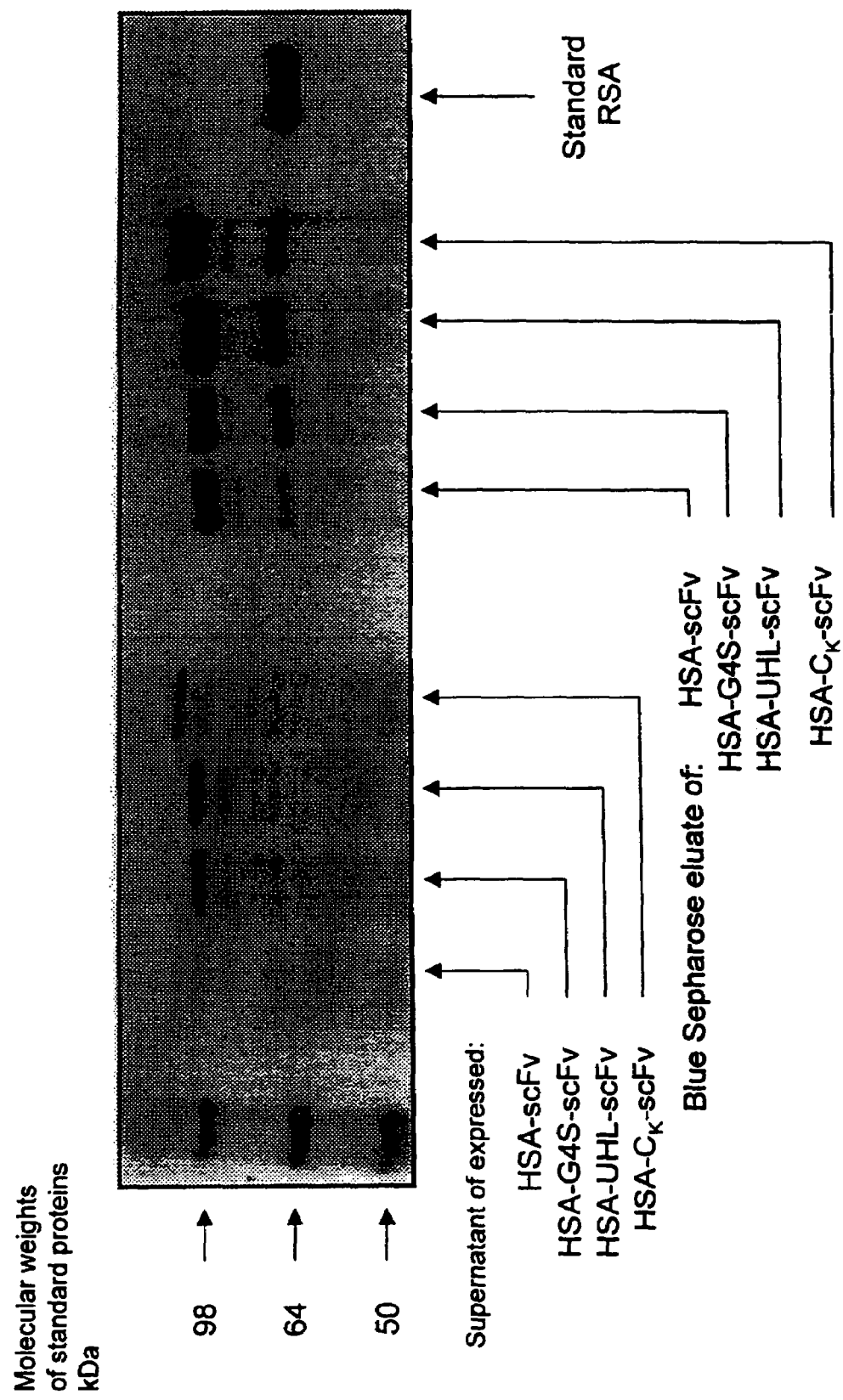
FIG. 5 Reducing SDS PAGE of HSA-scFv fusion proteins

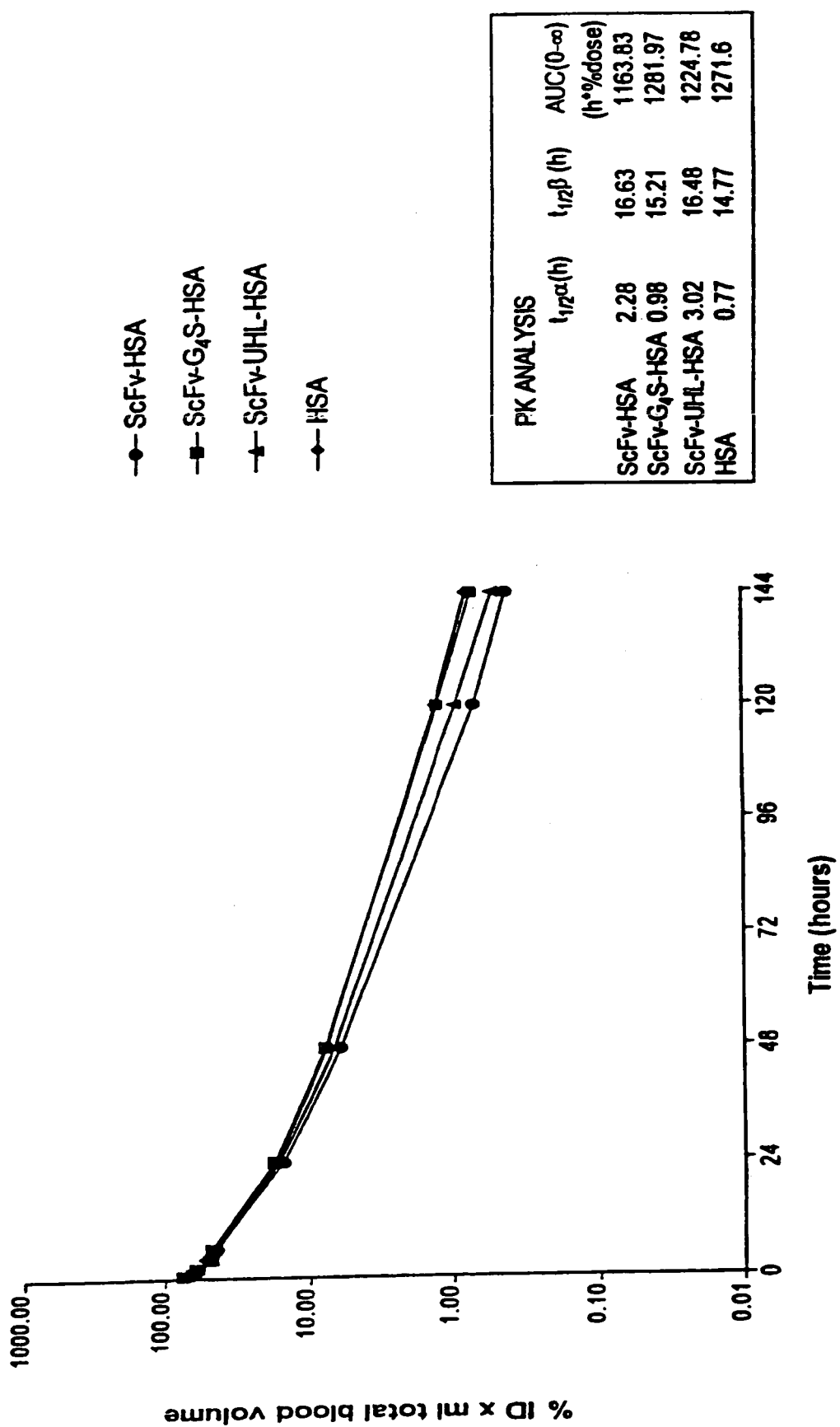
FIG. 6 Pharmacokinetics fo HSA-Fab' fusion proteins or HSA in the rat

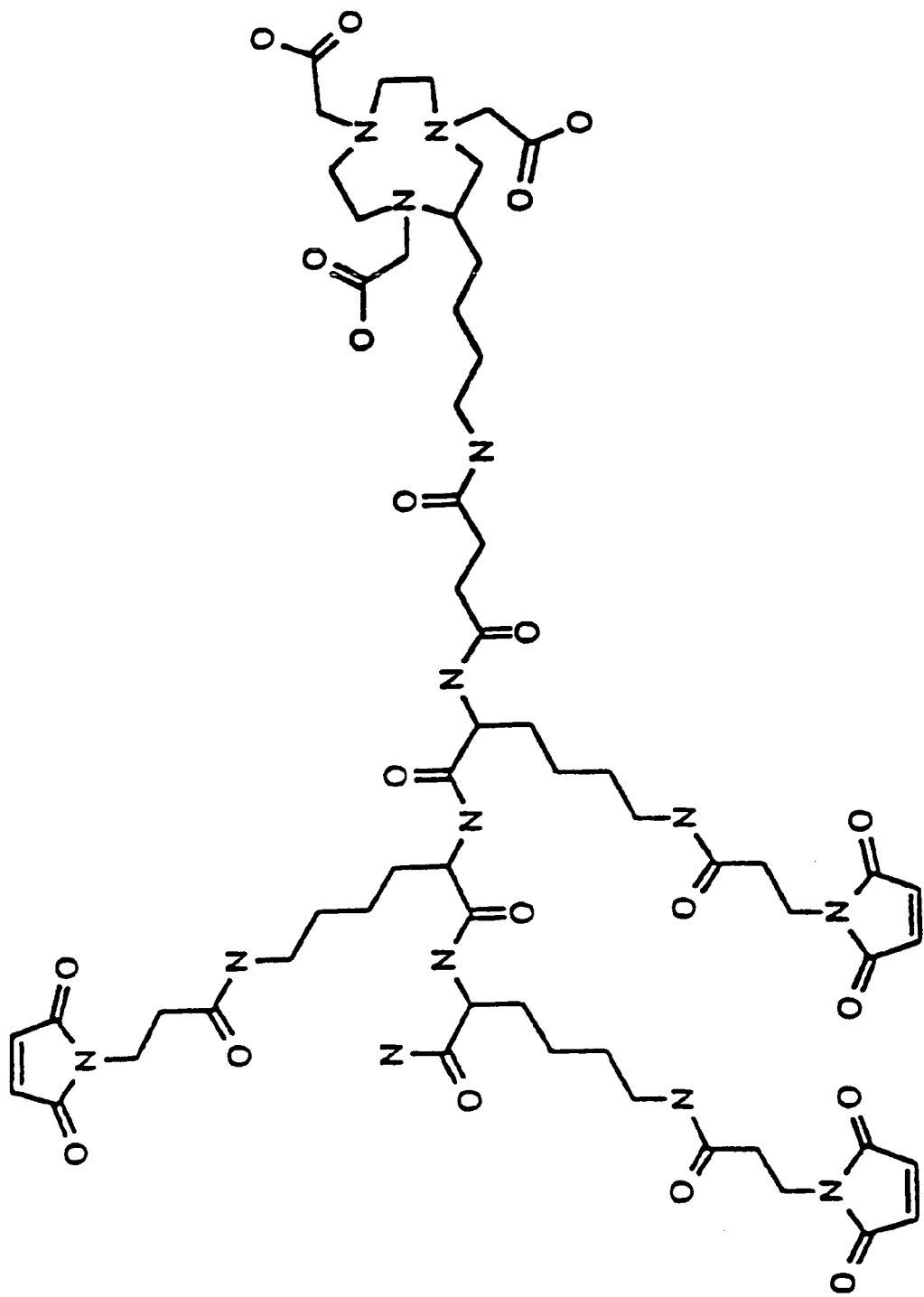
FIG. 7 Structure of trimaleimide crosslinking agent

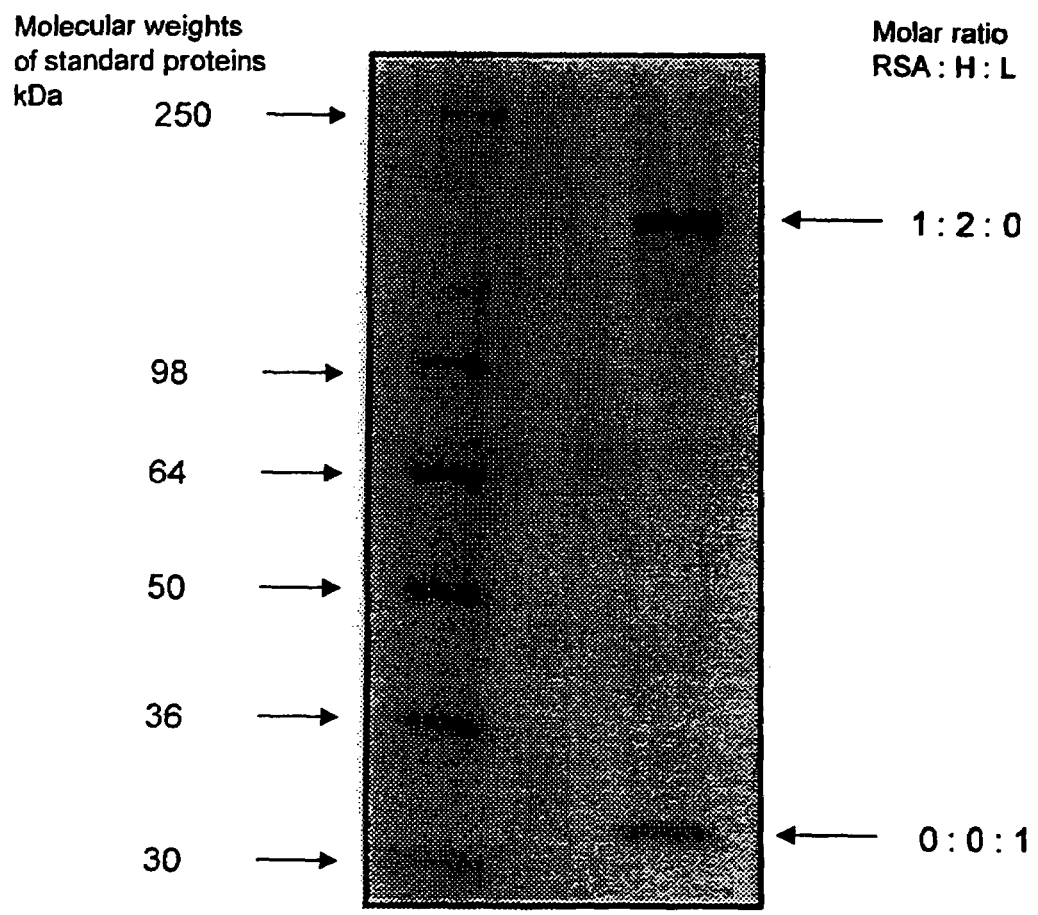
FIG. 8 Reducing SDS PAGE of HSA-F(ab')$_2$ conjugate

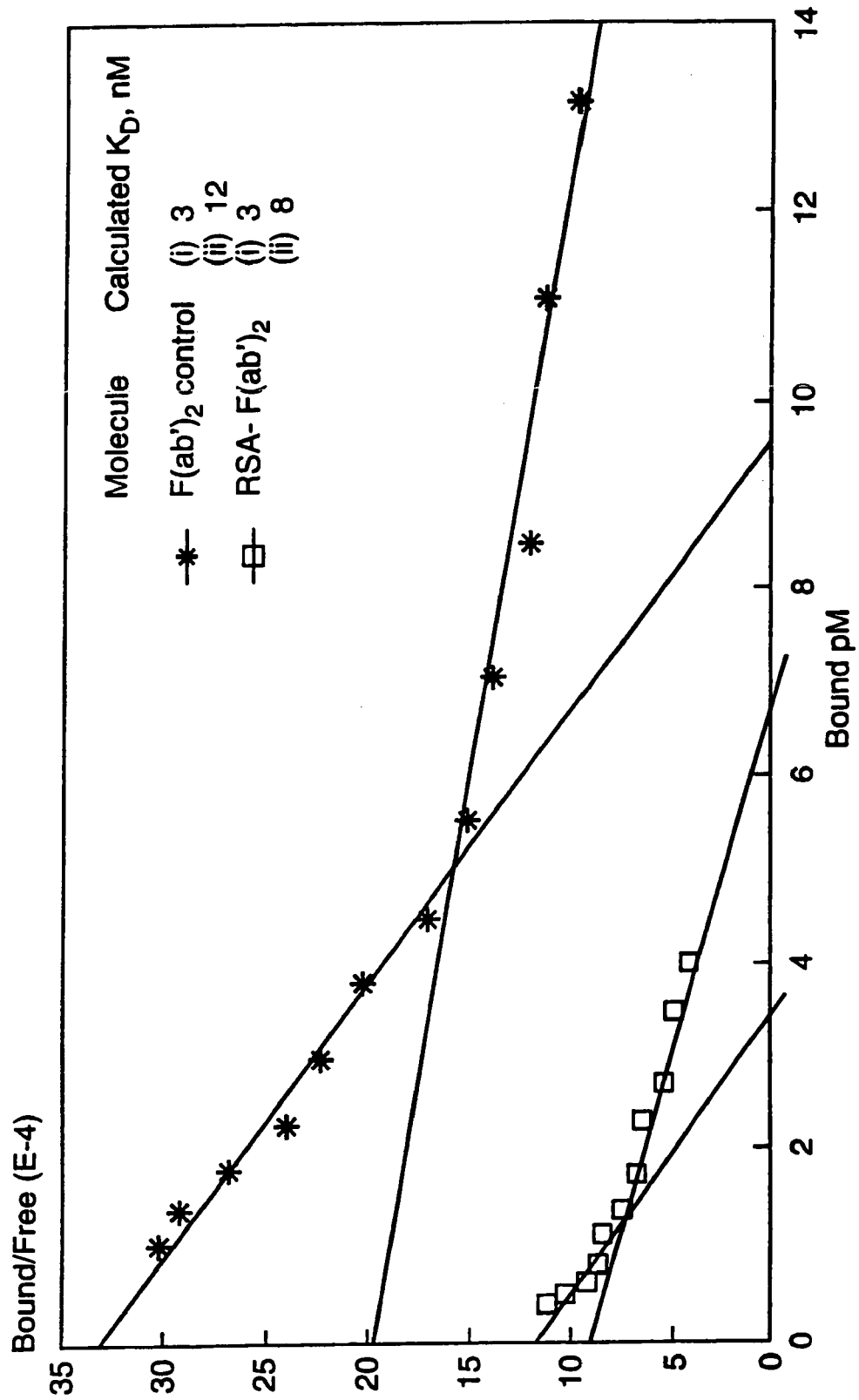
FIG. 9 Scatchard plots of binding of RSA-F(ab')$_2$ or F(ab')$_2$ control to cell membranes

ANTIBODY-SERUM PROTEIN HYBRIDS

This invention relates to modified antibody fragments, to processes for their preparation and to their use in medicine.

Since antibodies show great specificity in their binding to other molecules, they are of benefit as therapeutic or diagnostic agents, or as reagents (for example, as affinity purification reagents or as catalytic enzymes). The advent of hybridoma technology and the generation of transgenic animals has allowed the production of large volumes of monoclonal antibodies, sufficient for therapeutic use. Most such antibodies have been generated for treatment of acute diseases, such as particular types of cancer. For the treatment of chronic and/or more common diseases, still larger amounts of antibody are likely to be required. An increased usage also brings an increased need for a cheaper therapeutic agent.

Monoclonal antibodies can be produced in cultured mammalian or insect cells, or in transgenic animals, but the ability of these technologies to supply a large market at a reasonable cost, is unproven so far. Again, fungi have been shown to be able to produce heterologous proteins [e.g. Sleep, D., et al (1991) Bio/Technology, 9, 183–187], but expression of whole immunoglobulin G (IgG1) in a fungus has been reported to occur only at low level (in *Saccharomyces cerevisiae*), or in shakeflask culture (in *Pichia pastoris*), so antibody production from fungi on an industrial scale is unproven. [Horwitz, A. H., et al (1988) Proc. Natl. Acad. Sci. USA, 85, 8678–8682; Ogunjimi, A. A. et al (1999) Biotechnology Lett. 21, 561–567]. Furthermore, glycosylation of the antibody would be expected to be unlike that from mammalian systems, and in mammals this may generate problems of immunogenicity and abnormal function (complement activation, binding to Fc receptors, transcytosis and prolongation of half-life through interaction with FcRn receptor) [Nose, M. and Wigzell, H. (1983) Proc. Natl. Acad. Sci. USA, 80, 6632–6636; Tao, M.-H. and Morrison, S. L. (1989) J. Immunol. 143, 2595–2601; Wawrzynczak, E. J. et al (1992) Molec. Immunol. 29, 213–220; Kim, J.-K., et al (1994) Eur. J. Immunol. 24, 2429–2434].

Bacterial systems are not known to be capable of producing a whole, functioning antibody in a yield sufficient to give an economic process for large-scale manufacture, but they are a source of low-cost immunoglobulin fragments, such as Fab' [Better, M., et al (1988) Science, 240, 1041–1043]. Antibody fragments, however, may lack various of the functions of whole antibody. For example, Fab', F(ab')$_2$ or scFv lack the Fc domain that imparts a long lifetime in vivo: [Medesan, C. et al (1997) J. Immunol. 158, 2211–2217]. The half-life in circulation in mammals of Fab' or F(ab')$_2$ has been reported as being about 1% that of whole IgG [Waldmann, T. A. and Strober, W. (1969) Progr. Allergy, 13, 1–110.], and the β-phase half-life (the time taken for half of the molecules in circulation to be eliminated) of Fab' has been reported as being about 5% that of whole IgG [Chapman, A. P., et al (1999) Nature Biotechnology, 17, 780–783]. Thus, while they may be cheap to produce, these fragments are eliminated rapidly from circulation and can be of limited therapeutic use. This has led to attempts to prolong half-life of antibody fragments, for instance by modification of Fab' or F(ab')$_2$ in vitro by addition of one or more molecules of polyethylene glycol to each fragment molecule. International Patent Specification No. WO98/925971

In the present invention we have addressed the identifiable need for a means to economically produce an IgG fragment that can bind antigen and that has a long half-life in vivo. We have achieved this by employing a carrier protein to prolong the immunoglobulin in circulation.

Thus according to one aspect of the invention we provide a multi-component hybrid protein comprising one or more antigen-binding antibody fragments covalently linked to one or more serum carrier proteins or fragments thereof.

A variety of proteins exist in plasma, circulating in the body with half-lives measured in days, for example, 5 days for thyroxine-binding protein or 2 days for transthyretin [Bartalena, L. and Robbins, J. (1993) Clinics in Lab. Med. 13, 583–598], or 65h in the second phase of turnover of iodinated α1-acid glycoprotein [Bree, F. et al (1986) Clin. Pharmacokin. 11, 336–342]. Again, data from Gitlin et al. [Gitlin, D., et al (1964) J. Clin. Invest. 10, 1938–1951] suggest that in pregnant women the half-life of α1-acid glycoprotein is 3.8 days, 12 days for transferrin and 2.5 days for fibrinogen.

Serum albumin is an abundant protein in both vascular and extravascular compartments [Peters, Jr., T. (1985) Adv. Prot. Chem. 37, 161–245]. The half-life of albumin in man, about 19 days [Peters, 1985 ibid], is similar to that of IgG1 (about 21 days [Waldeman+Strober ibid], though it is less in other species—about 2 days in rats, for example [Peters, 1985 ibid]. Albumin does not possess the noted ability of antibodies to specifically bind ligands, particularly those of high molecular weight.

In the present invention we have produced a series of hybrid proteins that advantageously have the antigen-binding capabilities of an antibody fragment and the longevity of serum albumin in vivo. Additionally the hybrids may be especially suitable for use in expectant or nursing mothers since as with various other serum proteins, albumin is transported poorly across the placenta: labelled albumin injected into a mother appears with 5% or less specific activity in the foetus after 25 days [Gitlin, D. Kumate, J. Urrusti, J. and Morales, C. (1964) J. Clin. Invest. 10, 1938–1951]. This contrasts with IgG, which is transported efficiently across the placenta to the foetus. Similarly, albumin is not transported across the gut wall of neonates, whereas IgG is, by interaction with the FcRn receptor. Thus advantageously a foetus or neonate would be exposed to minimal amounts of the hybrids according to the invention from maternal circulation or milk.

With regard to commercial production, recombinant albumin has been reported as being produced at several gm per liter of culture of yeast (*Pichia pastoris* or *Kluyveromyces lactis* [Barr, K. A., et al (1992) Pharm. Eng. 12, 48–51; Fleer, R., et al (1991) Bio/Technology 9, 968–975; Cregg, J. M., et al (1993) Bio/Technology 11, 905–910]). This level of expression makes industrial production of pharmaceutical grade protein economically feasible, as remarked by Fleer et al [Fleer, R., et al (1991) Bio/Technology 9, 968–975]. Similarly, transgenic mice have been found to express as much as 10 gm per liter of albumin in their milk [Hurwitz, D. R, et al (1994) Transgenic Res. 3,365–375].

Depending on the intended specific use and/or half-life required, the hybrid protein according to the invention may be in a number of different forms. For example, one protein according to the invention may comprise an antibody fragment covalently linked to two, three or more serum carrier proteins or fragments thereof each of which may be the same or different. In another example, a protein according to the invention may comprise two, three or more antibody fragments, which may be the same or different, each covalently linked to the same serum protein or a fragment thereof. In general, however, a preferred hybrid protein according to the invention comprises one, two or three antigen-binding antibody fragments covalently linked to one serum carrier protein or a fragment thereof.

Each antigen-binding antibody fragment component in the proteins according to the invention will in general comprise an antibody variable region domain containing one or more antigen binding sites.

The variable region domain may be of any size or amino acid composition and will generally comprise at least one hypervariable amino acid sequence responsible for antigen binding embedded in a framework sequence. In general terms the variable (V) region domain may be any suitable arrangement of immunoglobulin heavy ($V_H$) and/or light ($V_L$) chain variable domains. Thus for example the V region domain may be monomeric and be a $V_H$ or $V_L$ domain where these are capable of independently binding antigen with acceptable affinity. Alternatively the V region domain may be dimeric and contain $V_H$-$V_H$, $V_H$-$V_L$, or $V_L$-$V_L$, dimers in which the $V_H$ and $V_L$ chains are non-covalently associated. Where desired, however, the chains may be covalently coupled either directly, for example via a disulphide bond between the two variable domains, or through a linker, for example a peptide linker, to form a single chain domain, e.g. scFv.

The variable region domain may be any naturally-occurring variable domain or an engineered version thereof. By engineered version is meant a variable region domain that has been created using recombinant DNA engineering techniques. Such engineered versions include those created for example from natural antibody variable regions by insertions, deletions or changes in or to the amino acid sequences of the natural antibodies. Particular examples of this type include those engineered variable region domains containing at least one CDR and optionally one or more framework amino acids from one antibody and the remainder of the variable region domain from a second antibody.

The variable region domain will in general be capable of selectively binding to an antigen. The antigen may be any cell-associated antigen, for example a cell surface antigen such as a T-cell, endothelial cell or tumour cell marker, or it may be an extracellular matrix antigen, an intracellular antigen or a soluble antigen. Particular examples of cell surface antigens include adhesion molecules, for example integrins such as β1 integrins, e.g. VLA-4, E-selectin, P-selectin or L-selectin, CD2, CD3, CD4, CD5, CD7, CD8, CD11a, CD11b, CD18, CD19, CD20, CD23, CD25, CD33, CD38, CD40, CD45, CDW52, CD69, carcinoembryonic antigen (CEA), human milk fat globulin (HMFG1 and 2), MHC Class I and MHC Class II antigens, and VEGF, and where appropriate, receptors thereof. Soluble antigens include interleukins such as IL-1, IL-2, IL-3, IL-4, IL-5, IL-6, IL-8 or IL-12, viral antigens, for example respiratory syncytial virus or cytomegalovirus antigens, immunoglobulins, such as IgE, interferons such as interferon-α, interferon-β or interferon-γ, tumour necrosis factor-α, tumour necrosis factor-β, colony stimulating factors such as G-CSF or GM-CSF, and platelet derived growth factors such as PDGF-α, and PDGF-β, and where appropriate receptors thereof.

In practice it is generally preferable that the variable region domain is covalently attached at a C-terminal amino acid to at least one other antibody domain or a fragment thereof. Thus, for example where a $V_H$ domain is present in the variable region domain this may be linked to an immunoglobulin $C_H1$ domain or a fragment thereof. Similarly a $V_L$ domain may be linked to a $C_K$ domain or a fragment thereof. In this way for example the fragment according to the invention may be a Fab fragment wherein the antigen binding domain contains associated $V_H$ and $V_L$ domains covalently linked at their C-termini to a CH1 and $C_K$ domain respectively. The CH1 domain may be extended with further amino acids, for example to provide a hinge region domain as found in a Fab' fragment, or to provide further domains, such as antibody CH2 and CH3 domains.

Each serum carrier protein component in the hybrid proteins according to the invention may be a naturally occurring serum carrier protein or a fragment thereof. Particular examples include thyroxine-binding protein, transthyretin, α1-acid glycoprotein, transferrin, fibrinogen and, especially, albumin, together with fragments thereof. The carrier proteins will in particular be of human origin. Where desired each may have one or more additional or different amino acids to the naturally occurring sequence providing always that the resulting sequence is functionally equivalent with respect to half-life. Fragments include any smaller part of the parent protein that retains the carrier function of the mature sequence.

The antibody and carrier protein components in the hybrid proteins according to the invention may be directly or indirectly covalently linked. Indirect covalent linkage is intended to mean that an amino-acid in an antibody fragment is attached to an amino-acid in a carrier protein through an intervening chemical sequence, for example a bridging group. Particular bridging groups include for example aliphatic, including peptide, chains as more particularly described hereinafter. Direct covalent linkage is intended to mean that an amino acid in an antibody fragment is immediately attached to an amino acid in a carrier protein without an intervening bridging group. Particular examples include disulphide (—S—S—) and amide [—CONH—] linkages, for example when a cysteine residue in one component is linked to a cysteine residue in another through the thiol group in each, and when the C-terminal acid function of one component is linked to the N-terminal amine of the other.

Particular bridging groups useful to indirectly link an antibody to a carrier protein include optionally substituted aliphatic, cycloaliphatic, heteroaliphatic, heterocycloaliphatic, aromatic and heteroaromatic groups. Particular groups include optionally substituted straight or branched $C_{1-20}$alkylene, $C_{2-20}$alkenylene or $C_{2-20}$alkynylene chains optionally interrupted and/or terminally substituted by one or more —O— or —S— atoms, or —N($R^1$)— [where $R^1$ is a hydrogen atom or a $C_{1-6}$alkyl group], —N($R^1$)CO—, —CON($R^1$)—, —N($R^1$)$SO_2$—, —$SO_2$N($R^1$)—, —C(O)—, —C(O)O—, —OC(O)—, —S(O)—, —S(O)$_2$—, aromatic, e.g. phenyl, hereroaromatic, e.g. pyridyl, or cycloalkyl, e.g. cyclohexyl groups. Such chains include for example optionally substituted straight or branched $C_{1-10}$alkylene chains such as optionally substituted butylene, pentylene, hexylene or heptylene chains, single amino acid residues and peptide chains, for example containing two to twenty amino acids, which may be the same or different, e.g. polyglycine chains such as (Gly)$_n$ where n is an integer from two to ten. Optional substituents which may be present on any of the above chains include one or more halogen atoms, e.g. fluorine, chlorine, bromine or iodine atoms, or $C_{1-6}$alkyl, $C_{1-6}$alkoxy, $C_{1-6}$haloalkyl, $C_{1-6}$haloalkoxy, —OH or —N($R^1$)($R^2$) [where $R^2$ is as defined for $R^1$] groups.

Where a bridging group indirectly links an antibody to a carrier protein the linkage may be to the side chain of any suitable amino acid, for example a lysine, arginine, serine, aspartic acid, glutamic acid or cysteine residue, located in the antibody or carrier protein. At each point of attachment the residue of a reactive group may be present. For example, where the bridging group is linked to a cysteine residue in the antibody or carried protein, the residue of a thiol-selective reactive group such as a maleimide group or the like may be incorporated as part of the attachment.

Where desired, the hybrid protein according to the invention may have one or more effector or reporter molecules attached to it and the invention extends to such modified proteins. The effector or reporter molecules may be attached to the antibody fragment and/or the carrier protein through any available amino acid side-chain or terminal amino acid functional group located in either component, for example any free amino, imino, hydroxyl or carboxyl group. The linkage may be direct or indirect, through spacing or bridging groups, as just described above, for linking the antibody and carrier protein components. Alternatively the reporter/effector may be attached to the linking moiety Effector molecules include, for example, antineoplastic agents, toxins (such as enzymatically active toxins of bacterial or plant origin and fragments thereof e.g. ricin and fragments thereof biologically active proteins, for example enzymes, nucleic acids and fragments thereof, e.g. DNA, RNA and fragments thereof, natural or synthetic polymers such as polysaccharides or polyalkylene polymers such as poly(ethylene glycol), radionuclides, particularly radioiodide, and chelated metals. Suitable reporter groups include chelated metals, fluorescent compounds or compounds which may be detected by NMR or ESR spectroscopy.

Particular antineoplastic agents include cytotoxic and cytostatic agents, for example alkylating agents, such as nitrogen mustards (e.g. chlorambucil, melphalan, mechlorethamine, cyclophosphamide, or uracil mustard) and derivatives thereof, triethylenephosphoramide, triethylenethiophosphor-amide, busulphan, or cisplatin; antimetabolites, such as methotrexate, fluorouracil, floxuridine, cytarabine, mercaptopurine, thioguanine, fluoroacetic acid or fluorocitric acid, antibiotics, such as bleomycins (e.g. bleomycin sulphate), doxorubicin, daunorubicin, mitomycins (e.g. mitomycin C), actinomycins (e.g. dactinomycin) plicamycin, calichaemicin and derivatives thereof, or esperamicin and derivatives thereof; mitotic inhibitors, such as etoposide, vincristine or vinblastine and derivatives thereof; alkaloids, such as ellipticine; polyols such as taxicin-I or taxicin-II; hormones, such as androgens (e.g. dromostanolone or testolactone), progestins (e.g. megestrol acetate or medroxyprogesterone acetate), estrogens (e.g. dimethylstilbestrol diphosphate, polyestradiol phosphate or estramustine phosphate) or antiestrogens (e.g. tamoxifen); anthraquinones, such as mitoxantrone, ureas, such as hydroxyurea; hydrazines, such as procarbazine; or imidazoles, such as dacarbazine.

Particularly useful effector groups are calichaemicin and derivatives thereof (see for example South African Patent Specifications Nos. 85/8794, 88/8127 and 90/2839).

Chelated metals include chelates of di-or tripositive metals having a coordination number from 2 to 8 inclusive. Particular examples of such metals include technetium (Tc), rhenium (Re), cobalt (Co), copper (Cu), gold (Au), silver (Ag), lead (Pb), bismuth (Bi), indium (In), gallium (Ga), yttrium (Y), terbium (Tb), gadolinium (Gd), and scandium (Sc). In general the metal is preferably a radionuclide. Particular radionuclides include $^{99m}$Tc, $^{186}$Re, $^{188}$Re, $^{58}$Co, $^{60}$Co, $^{67}$Cu, $^{195}$Au, $^{199}$Au, $^{110}$Ag, $^{203}$Pb, $^{206}$Bi, $^{207}$Bi, $^{111}$In, $^{67}$Ga, $^{68}$Ga, $^{88}$Y, $^{90}$Y, $^{160}$Tb, $^{153}$Gd and $^{47}$Sc.

The chelated metal may be for example one of the above types of metal chelated with any suitable polydentate chelating agent, for example acyclic or cyclic polyamines, polyethers, (e.g. crown ethers and derivatives thereof); polyamides; porphyrins; and carbocyclic derivatives.

In general, the type of chelating agent will depend on the metal in use. One particularly useful group of chelating agents in conjugates according to the invention, however, are acyclic and cyclic polyamines, especially polyaminocarboxylic acids, for example diethylenetriaminepentaacetic acid and derivatives thereof, and macrocyclic amines, e.g. cyclic tri-aza and tetra-aza derivatives (for example as described in International Patent Specification No. WO 92/22583); and polyamides, especially desferrioxamine and derivatives thereof.

Particularly useful hybrid proteins according to the invention include one or more antigen-binding antibody fragments covalently linked to one or more albumin molecules or fragments thereof.

Particular hybrids of this type include those wherein one antigen-binding antibody fragment is covalently linked to an albumin molecule or a fragment thereof. In these hybrids, and in general in the proteins according to the invention, each antigen-binding antibody fragment is preferably a monovalent Fab' fragment, optionally containing one or more additional amino acids attached to the C-terminus of the CH1 domain and is especially a Fab' fragment. Particularly useful Fab' fragments include those wherein the hinge domain contains a single cysteine residue. Fragments of albumin include one or more of domains I, II and/or III or subdomains thereof [see for example Peters, T. in "All about Albumin", Academic press, London (1996)].

Especially useful antibody-albumin hybrids according to the invention include those in which each protein component is directly linked through the C-terminal amino acid of the antibody to the N-terminal amino acid of the albumin. Where desired, one or more, e.g. up to around 100, additional amino acids may be inserted between the C- and N-termini to form a spacing group.

Another particularly useful class of antibody-albumin hybrids according to the invention is that wherein each protein component is indirectly linked between the thiol groups of a cysteine residue present in the antibody and another in the albumin. The indirect linkage may be achieved by a bridging molecule as described above. Particularly useful groups include non-cleavable linker groups, especially optionally substituted straight or branched $C_{1-10}$alkylene chains.

In this class of hybrids the antibody is preferably a Fab' fragment optionally containing one or more additional amino acids attached to the C-terminal of the CH1 domain. Especially useful fragments include Fab' fragments. The cysteine residue to which the spacing or bridging molecule is attached is preferably located in the CH1 domain of the Fab or, especially, is located in any C-terminal extension of the CH1 domain of the Fab, for example in the hinge domain of a Fab'.

The albumin in this class of hybrids may be in particular mature human serum albumin or a fragment thereof. In this instance, the bridging molecule may be attached to the cysteine residue at position 34 of the albumin. Advantageously, to avoid undesirable homodimer formation [see the Examples below] the bridging molecule may be from around 10 Å to around 20 Å in length, for example around 16 Å. Suitable bridging molecules in this length range may be easily determined from published sources, for example manufacturers' catalogues [see below]. Particularly useful bridging molecules include optionally substituted hexylene chains. Where each end of the bridging molecule is attached to the cysteine residue this may be through a disulphide bond or, in particular, a sulphur-carbon bond. Where the linkage is a sulphur-carbon bond, the residue of a thiol-selective reactive group, such as a maleimide, may be present as part of each end of the spacing or bridging group.

The hybrid proteins according to the invention may be useful in the detection or treatment of a number of diseases or disorders. Such diseases or disorders may include those described under the general headings of infectious disease, e.g. viral infection; inflammatory disease/autoimmunity e.g. rheumatoid arthritis, osteoarthritis, inflammatory bowel disease; cancer; allergic/atopic disease e.g. asthma, eczema; congenital disease, e.g. cystic fibrosis, sickle cell anaemia; dermatologic disease, e.g. psoriasis; neurologic disease, e.g. multiple sclerosis; transplants e.g. organ transplant rejection, graft-versus-host disease; and metabolic/idiopathic disease e.g. diabetes.

The hybrid protein according to the invention may be formulated for use in therapy and/or diagnosis and according to a further aspect of the invention we provide a pharmaceutical composition comprising a multi-component hybrid protein comprising one or more antigen-binding antibody fragments covalently linked to one or more serum carrier proteins or fragments thereof, together with one or more pharmaceutically acceptable excipients, diluents or carriers.

As explained above, the hybrid protein in this aspect of the invention may be optionally linked to one or more effector or reporter groups.

The pharmaceutical composition may take any suitable form for administration, e.g. for oral, buccal, parenteral, nasal, topical or rectal administration, or a form suitable for administration ny inhalation or insufflation, and preferably is in a form suitable for parenteral administration e.g. by injection or infusion, for example by bolus injection or continuous infusion. Where the composition is for injection or infusion, it may take the form of a suspension, solution or emulsion in an oily or aqueous vehicle and it may contain formulatory agents such as suspending, preservative, stabilising, antioxidant and/or dispersing agents.

Alternatively, the composition may be in dry form, for reconstitution before use with an appropriate sterile liquid.

If the composition is suitable for oral administration the formulation may contain, in addition to the active ingredient, additives such as: starch e.g. potato, maize or wheat starch or cellulose or starch derivatives such as microcrystalline cellulose; silica; various sugars such as lactose; magnesium carbonate and/or calcium phosphate. It is desirable that, if the formulation is for oral administration it will be well tolerated by the patient's digestive system. To this end, it may be desirable to include in the formulation mucus formers and resins. It may also be desirable to improve tolerance by formulating the antibody in a capsule which is insoluble in the gastric juices. It may also be preferable to include the antibody or composition in a controlled release formulation.

If the composition is suitable for rectal administration the formulation may contain a binding and/or lubricating agent; for example polymeric glycols, gelatins, cocoa-butter or other vegetable waxes or fats.

Therapeutic and diagnostic uses of hybrid proteins according to the invention typically comprise administering an effective amount of the protein to a human subject. The exact amount to be administered will vary according to the intended use of the protein and on the age, sex and condition of the patient but may typically be varied from about 0.1 mg to 1000 mg for example from about 1 mg to 500 mg. The protein may be administered as a single dose or in a continuous manner over a period of time. Doses may be repeated as appropriate. Typical doses may be for example between 0.1–50 mg/kg body weight per single therapeutic dose, particularly between 0.1–20 mg/kg body weight for a single therapeutic dose.

The hybrid proteins according to the invention may be prepared by standard chemical, enzymatic and/or recombinant DNA procedures.

Thus for example the hybrid protein may be prepared by the use of recombinant DNA techniques involving the manipulation and re-expression of DNA encoding antibody variable and/or constant regions and a desired carrier protein or a fragment thereof. Such DNA is known and/or is readily available from DNA libraries including for example phage-antibody libraries [see Chiswell, D J and McCafferty, J. Tibtech. 10, 80–84 (1992)] or where desired can be synthesised. Standard molecular biology and/or chemistry procedures may be used to sequence and manipulate the DNA, for example, to introduce codons to create cysteine residues, to modify, add or delete other amino acids or domains in the antibody and/or carrier protein as desired.

From here, one or more replicable expression vectors containing the DNA may be prepared and used to transform an appropriate cell line, e.g. a non-producing myeloma cell line, such as a mouse NSO line or a bacterial, e.g. *E. coli* line, or, especially, a fungal line, such as a yeast line, e.g. members of the genera *Pichia, Saccharomyces,* or *Kluyveromyces,* in which production of the antibody will occur. In order to obtain efficient transcription and translation, the DNA sequence in each vector should include appropriate regulatory sequences, particularly a promoter and leader sequence operably linked to the variable domain sequence. Particular methods for producing recombinant proteins in this way are generally well known and routinely used. For example, basic molecular biology procedures are described by Maniatis et al [Molecular Cloning, Cold Spring Harbor Laboratory, New York, 1989]; DNA sequencing can be performed as described in Sanger et al [PNAS 74, 5463, (1977)] and the Amersham International plc sequencing handbook; and site directed mutagenesis can be carried out according to the method of Kramer et al [Nucl. Acids Res. 12, 9441, (1984)] and the Anglian Biotechnology Ltd handbook. Additionally, there are numerous publications, including patent specifications, detailing techniques suitable for the preparation of proteins by manipulation of DNA, creation of expression vectors and transformation of appropriate cells for example as described in International Patent Specification No. WO86/01533 and European Patent Specification No. 392745.

Chemical synthesis of the hybrid proteins according to the invention may be achieved by coupling appropriately functionalised antibody, carrier protein and, where appropriate, bridging groups in a predetermined order. Standard chemical coupling techniques may be employed utilising starting materials containing one or more reactive functional groups such as thiols, acids, thioacids, anhydrides, acid halides, esters, imides, aldehydes, ketones, imines and amines. The starting antibody and carrier protein may be readily obtained from natural sources and/or by recombinant DNA techniques as described previously. Suitable bridging groups, for example in the 10 Å–20 Å length range as described above, are either commercially available [see for example Pierce & Warriner (UK) Ltd., Chester, UK] or may be obtained by simple functionalisation of known readily available chemical using convention chemistry.

Thus in one general approach, a homo- or heteropolyfunctional e.g. bi- or trifunctional bridging group, may first be coupled to either the antibody or carrier protein and the resulting product coupled as necessary to the remaining component(s) to provide the hybrid protein of the invention. The coupling reactions may be performed using standard conditions for reactions of this type. Thus for example the reaction may be performed in a solvent, for example an organic solvent, an aqueous-organic solvent or, especially, an aqueous solvent at or around ambient temperature up to around 70° C. Preferably, to avoid unwanted polymerisation in the first coupling reaction the homo- or heteropolyfunctional bridging group is employed in excess concentration relative to the antibody or carrier protein. Similarly in the second coupling reaction, the antibody or carrier protein is preferably employed in excess concentration to the product of the first coupling reaction. Illustrative reactions are described in detail in the Examples hereinafter for the preparation of proteins according to the invention and these may be readily adapted using different starting materials to provide other compounds of the invention.

The following Examples illustrate the invention. In these reference is made to various figures which are:

FIG. 1.

SDS PAGE of RSA-Fab' conjugate.

The RSA-Fab' conjugate was run under both reducing and non-reducing conditions. Approximate apparent molecular weights were estimated by comparison with standard proteins run on the same gel under reducing conditions. The molar ratios were determined by N-terminal sequencing of bands blotted from gels onto PVDF membrane.

FIG. 2.

Pharmacokinetics of RSA-Fab' conjugate or controls in the rat.

Proteins were $^{125}$I-labelled prior to injection into 6 rats. Radioactivity present in blood sample taken at intervals was quantified by gammacounting. Results of analysis by Winnonlin are shown. The units for the plasma half-life in α and β phases ($t_{1/2}\alpha$ and $t_{1,2}\beta$, respectively) are hours (h). The areas under the plasma concentration time curves (AUC, 0-∞) are in the units h*% dose. Data plotted as RSA-Fab' conjugate (correction factor) have been corrected from data for RSA-Fab' conjugate to allow for instability of labeled protein, as decribed in the text.

FIG. 3.

Pharmacokinetics of RSA-Fab' or Fab'-cys in the rat (assayed by ELISA or cytokine neutralisation).

Unlabeled proteins were injected into 2 rats, and subsequently quantified in samples of plasma by ELISA. In the case of the conjugate the ELISA employed binding of ligand (TNF) and of anti-albumin antibody, and in the case of the Fab'-cys control it employed binding of TNF and of anti-kappa L chain, as described in the text. The units for the plasma half-life in α and β phases ($t_{1/2}\alpha$ and $t_{1/2}\beta$, respectively) are hours (h). Alternatively, samples were assayed by neutralisation of TNF activity in the L929 assay. The areas under the plasma concentration time curves (AUC, 0-∞) are in the units h*% μg/ml. Curves for RSA-Fab' overlay each other, and curves for Fab'-cys do likewise. Error bars=s.e.m.

FIG. 4.

Construction of pPIC(scFv-HSA)

Flow chart of construction method.

FIG. 5.

Reducing SDS PAGE of HSA-scFv fusion proteins.

A sample of each fusion protein before and after Blue sepharose chromatography was run under reducing conditions, together with standard molecular weight markers and standard RSA on the same gel.

FIG. 6.

Pharmacokinetics of HSA-Fab' fusion proteins or HSA in the rat.

Proteins were $^{125}$I-labelled prior to injection into 6 rats. Radioactivity present in blood sample taken at intervals was quantified by gammacounting. Results of analysis by Winnonlin are shown. The units for the plasma half-life in α and β phases ($t_{1/2}\alpha$ and $t_{1/2}\beta$, respectively) are hours (h). The areas under the plasma concentration time curves (AUC, 0-∞) are in the units h*% dose.

FIG. 7.

Structure of trimaleimide crosslinking agent.

This reagent was used in generation of RSA-F(ab')$_2$ conjugate.

FIG. 8.

Reducing SDS PAGE of HSA-F(ab')$_2$ conjugate.

Purified sample and standard proteins were run on the same gel under reducing conditions. The molar ratios were determined by N-terminal sequencing of bands blotted from gels onto PVDF membrane.

FIG. 9.

Scatchard plots of binding of RSA-F(ab')$_2$ or F(ab')$_2$ control to cell membranes.

2 values for $K_D$ were calculated for each of the (biphasic) curves, as shown. Each phase of each curve is shown as a straight line

EXAMPLE 1

Fab'-Albumin Conjugate.

Methods

Preparation of Anti-TNF Fab'

Recombinant anti-TNF Fab' was produced in *E. coli*, and prepared from the periplasm by the methods described in International Patent Specification No. WO98/25971.

Conjugation of the Anti-TNF Fab' with Rat Serum Albumin

Rat serum albumin (RSA, fraction V, Sigma, code no. A-6272) was dissolved to 6.7 mg/ml (0.1 mM) in sodium acetate, 0.1M, pH5.9. Dithiothreitol solution (100 mM in the same acetate buffer) was added to give a final dithiothreitol concentration of 0.3M, so giving a 3-fold molar excess over RSA. The mixture was incubated at 37° C. for 40 min. The mixture was then subjected to chromatography on Sephadex G25M using a PD10 column (Pharmacia, code no. 17-0851-01, used as per manufacturer's instructions), thus removing dithiothreitol and exchanging the buffer for sodium phosphate, 0.1M, pH6, 2 mM ethylenediamine-tetraacetate (EDTA). The RSA concentration at that stage was 70 μM.

1,6 bismaleimidohexane (BMH, Pierce, code no. 22330) was dissolved to 7.736 mg/ml (28 mM) in dimethylformamide. The BMH solution was added to the reduced RSA solution to give a 21-fold molar excess of BMH over RSA. The mixture was incubated at 21° C. for 100 min, then subjected to chromatography on G25M in a buffer of sodium phosphate, 0.1M, pH6, 2 mM EDTA. The concentration of derivatised RSA was 46 μM at that stage.

The solutions of derivatised RSA and the anti-TNF Fab' (187 μM) in sodium phosphate, 0.1M, pH6, 2 mM EDTA were mixed to give a molar ratio, RSA:Fab':1:1.3 (which, corrected for derivatisation of RSA and reduction of Fab' thiol gave a ratio, derivatised RSA:reduced Fab':1:1.4). The mixture was incubated at 21° C. for 2 h, although reaction was essentially complete within 1 h. The mixture was then stored at 4° C. until subjected to purification procedures.

Conjugation of Fab' with Cysteine

The method for preparation of control molecule, anti-TNF Fab' covalently linked by BMH via thiols to cysteine (instead of RSA) was essentially the same as for preparation of conjugate (see above). 20 µM Fab' was reacted at 21° C. for 95 min with a 40-fold molar excess of BMH (added as a solution in dimethylformamide). After chromatography on G25M (to remove BMH) the derivatised Fab' was reacted with cysteine (Sigma, code no. C-4820) at a molar ratio Fab':cysteine free thiol:1:4.5. After reaction at 21° C. for 160 min, the sample was stored at 4° C. prior to purification of the Fab'-cys product.

Purification of the Conjugate

The reaction mixture was first subjected to chromatography on GAMMABIND™ PLUS SEPHAROSE™ (Pharmacia), a matrix that has affinity for Fab'. A 5.3 ml column was equilibrated in a buffer of sodium phosphate, 0.1M, pH6, 2 mM EDTA at a flow rate of 2 mL/min. All chromatography was at a temperature of 21° C. The sample was applied to the column at a flow rate of 1 ml/min, and the column then washed in the same buffer (sodium phosphate, 0.1M, pH6, 2 mM EDTA) until the baseline was restored. Adsorbed protein was eluted by application of a buffer of acetic acid, 0.5M, made to pH3 by addition of sodium hydroxide. The whole eluent was collected in fractions and each fraction analysed by SDS PAGE (using both reducing and non-reducing conditions). As expected of this affinity matrix, unconjugated Fab' eluted in the pH3 buffer, whereas the unconjugated RSA did not bind to the matrix at all, and emerged in the flow-through during sample loading. Conjugation of a single Fab' to one RSA molecule clearly affected its binding to the protein G on the matrix, for the conjugate emerged in the flow-through, just slightly later than (and overlapping with) the unconjugated RSA. The fraction containing the conjugate was subjected once more to chromatography on GAMMABIND™ PLUS SEPHAROSE™ (as above), in order to separate more RSA from it. The fractions containing conjugate (and some traces of RSA) were concentrated in a stirred cell (Amicon, 10 kDa nominal molecular weight cut-off membrane).

The contaminating RSA was removed from the preparation by gel permeation chromatography on a GF250 HPLC column of size 2×23 cm (using a Hewlett Packard 1090 HPLC). The column was equilibrated and eluted in a buffer of sodium phosphate, 0.2M, pH7, at a flow rate of 3 mL/min, at 21° C. The sample of concentrated conjugate (and RSA) was chromatographed and elution monitored at 280 and 220 nm. Fractions corresponding to observed peaks were collected and analysed by SDS PAGE. Those fractions containing the conjugate (which was completely resolved from the later-eluting RSA) were pooled and concentrated in a stirred cell (Amicon, 10 kDa nominal molecular weight cut-off membrane). The solution was stored at 4° C., with sodium azide added to 0.05% (w/v), to act as a preservative.

Purification of the Fab'-Cys

The reaction mixture containing Fab'-cys product was diluted 5-fold in a buffer of sodium acetate, 50 mM, pH4.5, then loaded onto a Mono S column (of 1 mL volume), using an FPLC (Pharmacia) apparatus. Adsorbed proteins were then eluted in a gradient of 0 to 250 mM sodium chloride in sodium acetate, 50 mM, pH4.5. Elution (1 ml/min at 21° C.) was monitored by absorption at 280 nm. Collected peaks were analysed by SDS PAGE.

Radiolabelling of Proteins

Proteins were labeled at the $\epsilon$-amino groups of lysyl residues, using $^{125}$I-labeled Bolton and Hunter reagent (Amersham International, code no. IM5861). Proteins were dissolved or diluted in a buffer of borate, to give a final borate concentration of 0.1M, pH8. A solution (of between 300 and 370 µL) containing 300 µg protein was then mixed with 20 µL Bolton and Hunger solution in propan-2-ol (containing 9 Mgq of $^{125}$I). The mixture was incubated at 21° C. for 15 min, then the reaction was quenched by addition of 60 µL solution of glycine, 1M, in borate, 0.1M, pH8.5. After approximately 5 min reaction at 21° C., the reaction mixture was chromatographed on SEPHADEX™ G25M using a PD10 column (Pharmacia, code no. 17-0851-01, used as per manufactuer's instructions). In doing so, the buffer was exchanged for phosphate buffered saline. The specific activity of each preparation was calculated from estimates of protein concentration (see Analytical Procedures) and of radioactivity, and were typically in the range 0.45 to 0.54 µCi/µg. The radiolabeled samples were used directly after labeling.

Analytical Procedures

Sodium dodecylsulphate polyacrylamide gel electrophoresis (SDS PAGE) utilised precast SDS gels (Novex), 1 mm thick and of acrylamide concentration 4 to 20%, run as per manufacturer's instructions. Gels were stained by soaking for 1 h in Coomassie BBG in perchloric acid (Sigma, code no. B-8772), followed by washing in water. Various molecular weight standards were used in order to derive approximate molecular weights (apparent) for sample proteins. These standards were Mark 12 and Seeblue unstained and prestained markers, respectively (Novex). For western blots, SDS PAGE was followed by blotting to polyvinylidene difluoride membrane (Millipore), with detection of the Fd fragment of the Fab' by sheep anti-human IgG(Fd) IgG fraction (The Binding Site, code no. PC075) followed by peroxidase-affinipure F(ab')$_2$ fragment of rabbit anti-sheep IgG, Fc fragment (Immunoresearch, code no. 313036046) and visualisation by use of chemiluminescence (ECL; Amersham International). For autoradiography, the SDS PAGE was followed by exposure of the gel to photographic film (Hyperfilm MP; Amersham International). For imaging of radiolabeled samples on gels (and subsequent quantification) the gels were exposed to high resolution or general purpose screens and processed in the Canberra Packard Cyclone system, using Optiquant software.

Quantification of protein solutions was by absorption at wavelength 280 nm in a 1 cm cell, using absorption coefficients (for 1 mg/mL solution in a 1 cm cell) of 1.43 for Fab' or F(ab')$_2$, and of 0.58 for RSA. A coefficient of 1.0 for RSA-Fab' conjugate was calculated from those of RSA and Fab', weighted in accordance with the constituent masses of the two components.

The concentration of free thiol in a protein solution was measured by adding ⅑ volume of 4,4'-dithiodipyridine (5 mM, final concentration therefore was 0.5 mM) in phosphate buffered saline. After 10 min at 21° C., the absorbency at 324 nm was measured in a 1 cm cell. The absorbency of a buffer-only blank sample was subtracted from this value, and this figure multiplied by 56.1167 to give the result in µM thiol (this being further corrected for any dilution of the original sample).

N-terminal protein sequencing was performed as per manufacturer's instructions on a model 470A protein sequencer with on-line 120A HPLC and 900A data analysis system (Applied Biosystems). Protein in solution was adsorbed to polyvinylidene difluoride membrane in a Prosorb device (Applied Biosystems). Proteins from SDS PAGE were blotted to polyvinylidene difluoride membrane (Immobilon PSQ, Millipore), and protein bands detected by staining by 0.1% (w/v) Ponceau S (Sigma, code no. P-3504)

in 1% (v/v) acetic acid for 1 min, then destaining the background in water. Bands were excised and sequenced directly.

Surface plasmon resonance study of interactions with ligand was performed on a BIACORE 2000 (Biacore AB), as per manufacturer's recommendations. Sensor chip surface coated by goat anti-human F(ab')$_2$ antibody (Jackson ImmunoResearch Lab. Inc.), which binds to the light chain, was used to bind conjugate, Fab' or IgG, whose binding to ligand (TNF) from solution was then measurable.

ELISA's were performed as follows below, with steps interspersed by washing in 0.1% Tween 20 in phosphate buffered saline. Microtitre plate wells were coated with cytokine antigen. Non-specific binding sites were then blocked by incubation of the wells with a 5% (w/v) solution of dried skimmed milk ("Marvel", Premier Beverages, UK) in phosphate buffered saline, for 1 h. Samples or standards were diluted in bovine serum albumin, 1% (w/v) in phosphate buffered saline, and then incubated in the wells for 1 h at 21° C. Quantification was by absorption at 630 nm, generated from 3,2'5,5' tetramethyl benzidine (120 µM in 10 mM acetate, pH6) as a result of the activity of peroxidase, following either of:

(i) For detection of albumin-Fab' conjugate, incubation of each well with rabbit anti-rat albumin (Cappel, product no. 55711, diluted 1 in 4000 in 1% bovine serum albumin in phosphate buffered saline), followed by goat anti-rabbit immunoglobulin Fc-peroxidase conjugate (Jackson, product no. 111-036-046, diluted 1 in 5000 in 1% (w/v) bovine serum albumin in phosphate buffered saline).

(ii) For detection of Fab', incubation in goat anti-human kappa light chain (Southern Biotechnology Associates, Inc., product no. 2060-01, diluted 1 in 5000 in 1% bovine serum albumin in phosphate buffered saline), followed by donkey anti-goat immunoglobulin (H+ L)-peroxidase conjugate (Jackson, product no. 705-035-147, diluted 1 in 5000 in 1% (w/v) bovine serum albumin in phosphate buffered saline).

Assay format (i) gave a linear response in the range 40–500 ng/ml of conjugate, and assay format (ii) gave a linear response in the range 5–100 ng/ml of Fab'

To assay the neutralisation of TNF activity, a monolayer of mouse L929 cells was grown in normal RPMI 1640 plus glutamine and 10% (v/v) foetal calf serum. TNF added in presence of actinomycin D (1%, w/v) with or without sample/anti-TNF. Cell death caused by TNF was monitored by MTT assay: 3-[4,5-Dimethylthiazol-2-yl]-2,5-diphenyltetrazolium bromide (MTT; Sigma, code no. M-2128) was added to a final concentration of 50 µg/ml in the medium of treated cells and incubated at 37° C. for 4 h. Reaction was stopped and the brown colour produced by live cells was solubilised by a solution of SDS, 20% (w/v) in 50% dimethylformamide in water, at pH4.7 (by addition of 50% acetic acid, 1M, in hydrochloric acid, 1M) and then quantified by measuring absorbance at 570 nm. Having subtracted the absorbance at 630 nm, the degree of cell survival (and so the concentration of active TNF present) could be assessed by comparison with samples of cells treated by standard amounts of TNF in the absence of TNF-neutralising activity.

Incubation of Protein in Plasma or Blood In Vitro

Rat plasma and blood (heparinised) were prepared fresh. To 100 µl was added 12 µl of $^{125}$I-labeled protein solution. Incubation was at 37° C. in a capped 0.5 ml tube, with 0.5 and 2 µL samples withdrawn at intervals for SDS PAGE and autoradiography.

Unlabeled conjugate or Fab'-cys (2 µl of 0.9 mg/ml solution) was mixed with 100 µl fresh rat plasma and incubated at 37° C. in a capped 0.5 ml tube. Samples of 21 µl were withdrawn at intervals for analysis by western blotting.

Pharmacokinetic Analysis of the Conjugate

Male Wistar rats (of approximately 250 g each) each received 20 µg of $^{125}$I-labeled, or 180 µg of unlabeled protein in solution in phosphate buffered saline, being injected into a tail vein. Samples of blood were taken from the tail artery at intervals thereafter, with plasma prepared by heparinisation and centrifugation. Samples were analysed as described above (see Analytical Procedures) and radioactivity in whole blood was calculated as cpm/g blood. The percent injected dose (% ID) was calculated for each individual rat, based on standards and expressed as % ID/ml total blood volume. Groups of 6 or 2 rats were used for study of $^{125}$I-labeled or unlabeled protein, respectively.

Data were analysed by WinNonlin software in order to determine the pharmacokinetic values quoted. A two compartment model was used for this analysis unless otherwise stated.

Results

Characterisation of the Conjugate

It is known that although serum albumin has one cysteinyl residue that is not engaged in a disulphide bond (residue 34 in the mature human albumin sequence), many of the molecules in a preparation of albumin do not possess a free cysteinyl thiol due to formation of mixed disulphides with molecules such as glutathione or free cysteine [Peters, ibid 1985]. In accordance with this, analysis of the rat albumin solution prior to reduction showed that there was 0.15 mole of thiol per mole of albumin, i.e. only 15% of albumin molecules possessed a free thiol. After reduction, this was increased to 0.95 mole of thiol per mole of albumin, consistent with presence of a free thiol group in 95% of albumin molecules, most likely at position 34 in the mature albumin sequence, since reduction under conditions such as those used here does not disrupt any of the disulphide present elsewhere in the molecule [Peters, ibid 1985]. Subsequent reaction at this cysteinyl residue allowed attachment of another molecule at a specific site, and in a 1:1 molar ratio, without concomitant production of other products of higher ratio of albumin:other molecule that would need to be removed subsequently. Co-ordinates for the crystal structure of human serum albumin have been deposited in the Brookhaven database (as entry 1AO6, by S. Sugio, S. Mochizuki and A. Kashima). Inspection of this model shows that the free cysteinyl residue at position 34 lies in a groove between two helices, but it is not clear from this how long a spacer arm on a crosslinking agent should be in order to work effectively. Absence of albumin homo-dimer would be advantageous in a production process since the yield of hetero-dimer then would be greater, and also there would be no need for an additional step to remove the homo-dimer. It was found that the cross-linking agent used in the present example produced this advantageous result. Reaction of the reduced albumin with a 20-fold molar excess of BMH caused derivatisation of 80% of these albumin molecules. Albumin homo-dimers were not formed during albumin derivatisation (or subsequent reaction with other protein molecules). The cross-linking agent spacer arm, of length 16.1 Å, was long enough to reach from the cysteinyl thiol at position 34 to the surface of the albumin molecule, where it was able to react with the free thiol on a Fab' molecule. It was not long enough to penetrate the equivalent groove on a second albumin to reach the free thiol there, and so production of homo-dimers was avoided.

The derivatised albumin and Fab' were mixed in the molar ratio 1:1.4:albumin:Fab'. SDS PAGE analysis of the products at the end of reaction indicated a yield of albumin-Fab' conjugate of the order of 20 to 30%, though this would be expected to be improved by optimisation of reaction conditions. The conjugate was purified from the reaction mixture by affinity chromatography, the conjugate surprisingly not binding to the matrix as did Fab', but eluting marginally later than did albumin, which did not bind at all. Having removed unreacted Fab', albumin was separated from the conjugate by size exclusion. The final preparation of conjugate was analysed by SDS PAGE (FIG. 1), which indicated (by apparent molecular weights) the linkage of one Fab' per albumin molecule. On non-reduced SDS PAGE the main band was a conjugate of 1 RSA with 1 Fab' molecule, as determined by N-terminal sequencing of the protein in the band. Approximately 37% of the conjugate was present as a higher molecular weight band that also had a RSA:Fab' ratio of 1:1. This was assumed to be dimer material, analogous to the observed occurrence of albumin polymers in untreated preparations of albumin. Lesser amounts (approximately 2% of total material) of conjugate missing L chain, and a putative small derivative of the conjugate (approximately 4% of total) were also present. N-terminal protein sequence analysis of the main band on reducing SDS PAGE showed it to be RSA-Fd (i.e. Fab' H chain), so that the linkage was specifically via the Fab' Fd and not via the L chain. Thus the 1:1 stoichiometry of conjugation, was confirmed.

Conjugation of Fab' to cysteine (to produce the control molecule, Fab'-cys) gave good yield—virtually all the Fab' derivative reacted with cysteine with only traces of F(ab')$_2$-like material of greater than approximately 55 kDa (apparent) on non-reducing SDS PAGE. This trace of material eluted just after the Fab'-cys product, which eluted at a sodium chloride concentration of about 75 mM on Mono S chromatography, and was excluded from it.

The ability to assay the conjugate in an ELISA that depended on the conjugate binding to TNF indicated that the conjugate retained the ability to bind TNF. This was confirmed by analysis of the conjugate binding to TNF by surface plasmon resonance using the BIACORE 2000 (association and dissociation rates, and equilibrium constant—see Table 1). This showed that the anti-TNF Fab' was unaffected by conjugation to albumin. This was also confirmed by its equal capacity for neutralisation of TNF: in an assay of L929 cell death caused by TNF the concentration of protein to inhibit 90% of TNF activity (the IC90) for the albumin-anti-TNF Fab' conjugate was 14.7 pM, as compared to 18.0 pM for anti-TNF Fab'-cysteine conjugate, 10.9 pM for anti-TNF F(ab')$_2$, and 11.3 pM for anti-TNF IgG4. The maintenance of Fab' binding activity was attributed to the intended orientation of the Fab' binding domain away from the point of conjugation to the albumin molecule, achieved by targeting of the Fab' hinge region as the point of attachment to the other moiety.

The control, Fab'-cys, also retained its ability to bind to, and to neutralise, TNF, as seen by its detection by ELISA and its activity in the L929 assay.

Pharmacokinetic Analysis of the Conjugate in Rat Plasma $^{125}$I-labeled RSA, Fab', F(ab')$_2$ and RSA-Fab' conjugate were monitored in plasma sampled at various times over 144 h (FIG. 2). The observed β-phase half-life of albumin was in agreement with the literature value of about 2 days [Peters, ibid 1985]. The β-phase half-life of the F(ab')$_2$, and the Fab', were similar to that of F(ab')$_2$ described previously [e.g. Kitamura et al, ibid; Chapman et al, ibid], and was preceded by rapid elimination in the α-phase, typical of such molecules. However, when the Fab' was conjugated to RSA it persisted in circulation in the rat to a degree comparable to rat albumin. Due to a reduction of elimination during both α- and β-phases, the conjugate showed a 35-fold greater area under the plasma concentration curve (AUC, 0-∞) than did the Fab'-cys control, similar to that of albumin alone. In order to ensure that radioactivity detected in the plasma samples reflected remaining conjugate, samples from one rat given labeled conjugate were run on SDS PAGE and scanned by phosphorimager (data not shown). This showed the persistence in vivo of intact labeled conjugate for at least 120 h, and the β-phase half-life of intact conjugate was calculated to be 32.07 h, in good agreement with the equivalent result from total $^{125}$I detection.

The stability of the conjugate in plasma was inspected. Incubation of the unlabelled conjugate in rat plasma (in vitro) at 37° C. for 68 h in the presence or absence of a variety of protease inhibitors, monitored by SDS PAGE and western blotting, indicated that the conjugate was stable in rat plasma. Conjugate that had been labeled by $^{125}$I was incubated in vitro in phosphate buffered saline (pH7) for up to 10 days and was also found to be stable.

However, incubation of the $^{125}$I-labeled conjugate at 37° C. in rat plasma or blood in vitro indicated that the molecule was not completely stable, some molecules suffering cleavage at or near the point of linkage between the albumin and the Fab' molecule. Since unlabeled conjugate was stable, the observed instability was attributed to modification of the protein by the presence of $^{125}$I or by the labeling process. Despite an apparent instability in these conditions, intact material remained even after 168 h incubation in vitro. The integrity of the conjugate in vivo was assessed by SDS PAGE of plasma samples, followed by quantification of the intact conjugate by phosphorimager scanning, and as in experiments in vitro, a small instability of $^{125}$I-labelled conjugate was noted. The observed results from in vivo experiments could be adjusted accordingly to reflect the quantity of intact, labeled conjugate only. The adjusted data gave the result shown in FIG. 2 (see conjugate (correction)), which was that even the slightly unstable labeled version of the conjugate had an AUC that was 17-fold greater than the Fab'-cys control.

The conclusion that data derived from the use of $^{125}$I-labeled conjugate represent an underestimate of the longevity of the unlabelled conjugate in vivo was supported by an experiment in which the conjugate was not labelled. Unlabeled protein was monitored by two forms of ELISA and by biological activity (TNF neutralisation in the L929 assay). Results from use of the three assays in samples from two rats were similar to each other (FIG. 3), showing that RSA-Fab' was stable in vivo for protracted periods. However, Fab'-cys was eliminated rapidly, such that too few data were obtained by ELISA to allow use of a two compartment model, and the AUC estimate given in FIG. 3 is by use of a one compartment model. Too few data were obtained by use of activity assay to allow any modeling at all. The RSA-Fab'conjugate's AUC was about 200-fold greater than that of the Fab'-cys control.

It has been shown that it is possible to prepare an IgG antibody Fab' fragment, chemically crosslink it to albumin in vitro with retention of full binding ability (having the same affinity as seen in the whole antibody), and demonstrate that it has a significantly longer half-life in vivo than does the unconjugated Fab'. The conjugate contained one Fab' per albumin molecule. The β-phase half-life of the conjugate in the rat was about twice that of the unconjugated Fab, being closer to that of unconjugated albumin, and the area under the curve was about 200-fold greater for the conjugate than for the unconjugated Fab'. Thus, the consequence of conjugation of Fab' to albumin was a significant prolongation of its biological activity in vivo, allowing (in the present case) prolonged anti-cytokine therapy.

EXAMPLE 2

Genetic Fusion of scFv to Albumin

Methods

Construction of Plasmids Coding for scFv-Human Serum Albumin Fusion Proteins.

Plasmid pPIC(scFv) contained the gene for an anti-TNF scFv, comprising the variable domains in the order $V_L$-$V_H$. This plasmid was cleaved with restriction enzymes Kpnl and Notl to generate a 'vector' DNA fragment which was purified following agarose electrophoresis. Into this was ligated a Pvull-Notl fragment of DNA containing the mature HSA gene, together with a 200 bp linker encoding a direct in-frame fusion between the C-terminus of the scFv and the N-terminus of HSA. This procedure is summarised in FIG. 4. The linker or junction fragment also introduced a unique Clal restriction site to facilitate the construction of a further series of genes encoding fusion proteins containing different spacers to physically separate the scFv and HSA motifs. Annealed oligonucleotide cassettes were used to introduce the following spacers between the Kpnl and Clal sites:
1. A sequence encoding 3 repeats of the $Gly_4Ser$ sequence.
2. A sequence derived from the flexible N-terminal end of the human IgG1 hinge region.

In addition, a gene encoding a further fusion protein was generated in which the C-domain from human Ig-kappa light chain was used as a spacer to separate the scFv (this time in the $V_H$-$V_L$ orientation) from the HSA. The construct nomenclature was: scFv-HSA; scFv-G4S-HSA; scFv-UHL-HSA; scFv-$C_K$-HSA, respectively.

Expression of Fusion Proteins in Yeast.

These plasmids were linearised and transfected into competent *Pichia pastoris* cells. This was done using an "EasySelect *Pichia* Expression" kit (Invitrogen) by following the manufacturer's instructions. Transformants were selected by resistance to Zeomycin (500 g/ml) incorporated in the YPDS agar used to grow them. Transformants were confirmed as being Mut⁺, that is, capable of utilising methanol as the sole carbon source, though sensitive to the presence of excess methanol. Two colonies of each of the 4 types of transformant were picked and grown in shake flask culture in BMGY medium, as per "EasySelect *Pichia* Expression" kit instructions. Each culture was 25 ml in a 25 ml flask, incubated at 30° C., shaking at 225 rpm. After 16–18 h, when the cultures had grown to give an optical density at 600 nm (OD600) of between 2 and 6, cells were harvested by centrifugation and resuspended in 30–40 ml of BMMY medium (which contains methanol as carbon source), to give an OD600 of 1. Incubation was then continued with shaking and occasional addition of methanol in order to maintain a methanol concentration of approximately 0.5% (v/v). After 84 h incubation the cultures were centrifuged and the supernatants retained for use in preparation of expressed and secreted fusion proteins.

Purification of Fusion Proteins.

Expressed proteins were purified from the yeast culture medium after clarification by centrifugation. The medium was subjected to chromatography on a matrix of Blue sepharose (Pharmacia), which acted as an affinity matrix for albumin-containing proteins, as follows below. Each clarified supernatant was mixed with one volume of phosphate buffered saline, pH7, and the pH of the mixture increased from about 6.5 to about 7 by addition of a small volume of sodium hydroxide solution (2M). The mixture was then applied to a 1.5 ml column of Blue sepharose, pre-equilibrated in phosphate buffered saline, pH7. The flow rate at all stages was 0.5 ml/min, and the temperature was 21° C. Following application, the column was washed by phosphate buffered saline until a stable baseline was achieved, and then bound protein was eluted by the eluent sodium thiocyanate, 0.2M in phosphate buffered saline. Elution was monitored by absorbtion at 280 nm wavelength. Eluted protein was collected, concentrated, and its buffer exchanged to phosphate buffered saline by use of a stirred cell concentrator (Amicon, using a 10 kDa nominal molecular weight cutoff filter membrane). Protein was quantified by absorbance at a wavelength of 280 nm and use of theoretical absorbtion coefficient that was calculated for each fusion protein by use of the program ProtParam (found at the ExPasy website).

Radiolabeling of Proteins

Fusion proteins with no linker, with G4S linker or with upper hinge linker, and unmodified human serum albumin were labelled by $^{125}I$ as described in Example 1, above.

Analytical Procedures

Proteins were characterised and their pharmacokinetics in rats analysed as described in Example 1.

Results

Characterisation of Fusion Proteins

All four scFv-human serum albumin (HSA) fusion proteins were expressed from *Pichia pastoris*, being secreted into the medium at the following rates, as determined by absorbance at 280 nm of protein solutions prepared by chromatography (mean of 2 experiments): scFv-HSA (no linker), 9.0 µg/ml; scFv-G4S-HSA, 8.5 µg/ml; scFv-UHL-HSA, 7.5 µg/ml; scFv-$C_K$ linker, 7.8 µg/ml. Bands corresponding to the expressed proteins could be seen upon SDS PAGE of unfractionated yeast culture medium (e.g. FIG. 5). No development was undertaken with the aim of improving expression levels. These data suggested that the order of the variable domains in the scFv portion did not significantly affect the levels of expression of the fusion protein.

Reducing SDS PAGE (FIG. 5) of prepared fusion proteins after only Blue sepharose chromatography showed each to contain one principle band and one minor, where the major species accounted for 91% of all protein in the scFv-HSA preparation, 75% in the scFv-G4S-HSA preparation, 80% in the scFv-UHL-HSA, and 83% in the scFv-$C_K$-HSA preparation, as estimated by scanning of brilliant blue G-stained gels. The principle band in each preparation had an apparent molecular weight equal to the theoretical molecular weight calculated from the translated DNA sequence. The minor band in each migrated with standard human serum albumin on the same gel, indicating minor cleavage event(s) at the sequence between albumin and scFv or scFv-hinge/spacer sequence. N-terminal sequencing of this minor product in the scFv-G4S-HSA preparation showed that it did indeed have the N-terminus of mature HSA. N-terminal sequence analysis of the fusion proteins showed them to have the expected scFv N-terminus, in each case preceded by the sequence EAEA, which had been included in the fusion protein in order to alleviate possible problem(s) of steric hindrance rendering the cleavage of the pro-sequence inefficient (as discussed by Sreekrishna, K. et al (1997) Gene, 190, 55–62). This EAEA spacer sequence was not subsequently removed by yeast diaminopeptidase activity, however. Nevertheless, this N-terminal EAEA extension did not obviously inhibit expression and secretion of the heterologous proteins. It is likely that the EAEA sequence could be deleted from the fusion protein in order to generate a protein of authentic scFv (or other) N-terminus.

Blue sepharose chromatography was shown to be efficient in purification of albumin-containing proteins in a single step. These proteins included minor products of proteolysis in the present cases, but no optimisation was undertaken here. Thus, proteolysis would be expected to be reduced by such means as optimisation of culture conditions, inclusion of protease inhibitors, and/or expression in protease-deficient strains of yeast (for instance, as described by Gleeson, M. A. G. et al in "*Pichia* Protocols" [eds. Higgins, D. R. and Cregg, J. M.), pub. Humana Press, Totowa, N.J. (1998), pp 81–94]. In terms of industrial processes, the cost of Blue sepharose is very low, certainly considerably lower than any other commercially-available affinity matrix. Thus, the use of albumin as part of a fusion protein is doubly beneficial, since it can not only add to the protein such properties as long serum half-life (see Example 1 or below), but also allow rapid, low cost purification. The ability of the fusion proteins to bind ligand was confirmed by Biacore analysis. This showed that the association and dissociation rates and $K_D$ of the 4 types of fusion protein were similar to each other and to other forms of the anti-TNF antibody, including whole IgG (Table 1).

Pharmacokinetic Analysis of the Fusion Proteins in Rat Plasma

The fusion proteins scFv-HSA, scFv-G4S-HSA and scFv-UHL-HSA were $^{125}$I-labelled, as was HSA alone. The minor component of albumin that was present in each of the fusion protein preparations became labeled, too.

Analyses of the distribution of label in the in the fusion protein and albumin components of the preparations by the two methods of autoradiography and by phosporimaging gave similar results. The mean of the two methods was: for scFv-HSA, 76% of label was in the fusion protein; for scFv-G4S-HSA, 80% of label was in the fusion protein; for scFv-UHL-HSA, 40% of label was in the fusion protein. Remaining label was taken up by the albumin component of each preparation.

These proteins were injected into rats (n=6). Plasma samples were taken at intervals for analysis by gamma counting and by SDS PAGE followed by phosphorimaging. The distribution of label in the different samples were determined during the first 48 h by phosphorimaging of samples from one rat per group (replicate number, n=2 or 4). In each case there was found to be no clear change in the distribution of label during the 48 h period (data not shown). Therefore, the fusion proteins were not prone to significant degradation in vivo. It was assumed that this stability was maintained for the full duration of the experiment, which was 144 h, and the pharmacokinetic analysis of the proteins was based on the results of gammacounting. The pharmacokinetics were similar for all proteins (see FIG. 6), thereby showing that the fusion proteins behaved similarly to unmodified human albumin in plasma in vivo. Note that in rats HSA is only a half (or less) as persistent as the homologous, rat, albumin, and a fusion of scFv with HSA would not necessarily be expected to endow a half-life any longer than that of HSA itself. Nevertheless, the AUC for the $^{125}$I-fusion proteins are approximately 13-fold greater than those for $^{125}$I-Fab'-cys control (shown in FIG. 2).

This example shows that serum albumin may be fused to another protein(s) to generate a fusion that possesses function(s) of the other protein(s) together with the long half life of albumin. Furthermore, since fusion did not involve albumin cysteinyl thiols, the possibility remains of using a fusion protein as an acceptor of one or more Fab' molecules, linked by chemical means, as exemplified by Examples 1 and 3. Polyspecific as well as polyvalent molecules could be generated in these ways.

EXAMPLE 3

Fab' Dimer-Albumin Conjugate.
Methods.
Preparation of the Dimer of Anti-Cell Surface Marker Fab'.

The anti-cell surface marker was engineered as a Fab'. It was expressed in *E. coli* and was extracted from the periplasm, as described in International Patent Specification No. WO98/25971.

The Fab' interchain disulphide bond was reduced as follows: 12 ml of Fab' at 20.93 mg/ml in 0.1M sodium phosphate, pH6.0, 2 mM EDTA was mixed with 240 µL 250 mM 2-mercaptoethylamine in the same buffer, and incubated for 50 min at 38° C. Diafiltration of the sample against the same buffer removed the reducing agent. The yield of Fab' at this stage was 85.1%. Thiol assay showed there to be an average of 0.83 free thiols per Fab' molecule, and analysis by GF250 size exclusion chromatography indicated the protein to comprise 93.1 Fab' monomer and 6.9% disulphide-bonded $F(ab')_2$.

The crosslinking agent was a trimaleimide compound, illustrated in FIG. 7. This molecule also contained a metal-chelating function. A 1 mg/ml solution of this compound was made in 0.1M sodium phosphate, pH6.0, 2 mM EDTA, and 5 aliquots of 434.8 µl each added with mixing at 5 min intervals to the above reduced Fab' preparation. This provided a molar ratio crosslinker:Fab':1:2.56. The mixture was incubated at 21° C. for 3 h, at which time 25 µl glacial acetic acid was added to lower the pH to 4.5. 47 ml water was added to lower conductivity and the mixture resolved by ion exchange chromatography. The proteins were applied to a 2.6 cm i.d.×15.5 cm column (Pharmacia) containing methyl sulphonate cation exchanger (SP-Sepharose HP) at a flow rate of 10.5 ml/min, and eluted by a gradient of 0 to 250 mM sodium chloride in 50 mM acetate, pH4.5. Elution was monitored by absorbance at 280 nm. The various reaction products (monomer, dimer, and trimer) were identified by SDS PAGE and by GF250 size exclusion chromatography. Only that fraction containing dimer Fab' was used for the subsequent conjugation to albumin.

Linkage of Fab' Dimer to Rat Serum Albumin.

33.71 mg of RSA was dissolved in 2.5 ml of 0.1M sodium phosphate, pH6.0, 2 mM EDTA and mixed with 25 µL of 200 mM 2-mercaptoethylamine in the same buffer, giving a final reducing agent concentration of 2 mM. The mixture was incubated at 37° C. for 1 h. Reducing agent was then removed by size exclusion chromatography on Sephadex G25M, using a PD10 column (Pharmacia, code no. 17-0851-01, used as per manufacturer's instructions. The buffer was then sodium phosphate, 0.1M, pH6, 2 mM (EDTA). The concentration of albumin was 143 µM.

The reduced albumin was incubated with conjugated Fab' dimer in a molar ratio of 1:1, and incubated at 21° C. for 24 h. The reaction mixture was resolved by chromatography on Gammabind plus, as described in example 1 (above), using a column of 3 ml volume. Unreacted albumin failed to bind to this matrix. Bound material was eluted by a buffer of 0.5M acetic acid, pH3. Eluted fractions were immediately neutralised by addition of trizma, 2M, pH 8.8. This material was further purified by Blue sepharose chromatography, as described in Example 2. Unreacted Fab' dimer failed to bind to the matrix, and bound material was eluted by sodium thiocyanate, 0.2M in phosphate buffered saline. Eluted fractions were concentrated and the buffer exchanged for phosphate buffered saline in a stirred cell (Amicon) with a 10 kDa nominal molecular weight cutoff filter. Each type of chromatography was repeated in order to completely purify the albumin-Fab' dimer conjugate.

Analytical Procedures.

Procedures were as described in Examples 1 and 2, except that for N-terminal protein sequence determination, the automated sequencer used was a PE Biosystems Procise 492. Additionally, the ligand binding characteristics of the conjugate were determined by Scatchard analysis of its binding to whole cells, as follows below.

The conjugate and a control protein (a dimer of Fab' crosslinked through thiols by bis-maleimido hexane) were labelled by attachment of fluorescein. This was done by incubation of one mg protein in 1 ml of 0.1M $NaHCO_3$ with 100 μg fluorescein isothiocyanate (Sigma F7250) added as 10 μl solution in dimethyl sulphoxide. Reaction was for 2 h at 21° C. The reaction was stopped by addition of a molar excess of lysine. Labelled protein was separated from free fluorescein by size exclusion chromatography. The fluorescein-labelled antibody was collected in phosphate-buffered saline, and the protein component quantified by absorption at 280 nm, while the extent of substitution was estimated from absorption at 495 nm. The μM extinction coefficient used for DFM was 0.14, for RSA-(Fab')$_2$ was 0.2 and for fluorescein was 0.077. The fluorescein-labelled control protein had a fluorescein:protein molar ratio of 1.59, and the fluorescein-labelled RSA-(Fab')$_2$ had 3.08 fluorescein molecules per protein molecule.

The fluorescent protein conjugates were then serially diluted (1:1.4) from a top concentration of 2 μg/ml in phosphate buffered saline containing 5% (v/v) foetal calf serum. The final volume per tube was 250 μl. Forty thousand target cells were added in 100 μl per tube to give a final volume of 350 μl and a final highest antibody concentration of 1.43 μg/ml. Cells were incubated with antibody at 4° C. for 3 h. Fluorescence activated cell sorting (FACS) analysis was then performed on the cells. Fluorescence signal was converted to molecules of equivalent soluble fluorescein from a standard curve of fluorescent beads according to the method of Krause et al., (1990) Determination of Affinities of Murine and Chimeric Anti-α/β-T Cell Receptor Antibodies by Flow Cytometry. Behring Inst. Mitt. 87,56–67). The number of molecules of fluorescein bound per cell was converted to the number of molecules of antibody bound per cell by the fluorescein:protein ratio. Subtraction from the total number of antibody molecules per tube gave the number of molecules free per tube. Scatchard analysis was performed on these data.

Results.

In the non-optimised conditions used, the yields of products from the chemical crosslinking reaction were: Fab' trimer, 30.6%; Fab' dimer, 30.7%; Fab' monomer, 38.7%.

This dimer was used in subsequent reactions with albumin. Being produced by crosslinking with a tri-functional agent, the dimer possessed one functional group remaining on the linking moiety. This was a maleimide that was able to react with a free thiol. A free thiol was generated in rat albumin by reduction, by a method that was different from that used in Example 1. Assay of thiols in the albumin preparation reduced in this way showed that there was then an average of 0.97 free thiols per molecule. Thus, a single thiol may be generated in albumin by more than one method.

Incubation of the prepared Fab' dimer with the reduced RSA gave a yield of 1 mg of albumin-Fab' dimer conjugate, as estimated by absorbance at 280 nm, using a theoretical absorption coefficient calculated by the program ProtParam (ExPasy), after complete purification.

SDS PAGE (reduced) of the product showed the presence of two bands, of apparent molecular weight of approximately 150 kDa and approximately 31 kDa (FIG. 8). N-terminal sequencing showed these to be albumin-Fab' heavy chain dimer, and Fab' light chain, respectively. Non-reduced SDS PAGE showed one main band of apparent molecular weight about 200 kDa. N-terminal protein sequencing showed this band to be albumin-Fab' (i.e. heavy plus light chains) dimer. That the product of combination of RSA and Fab' dimer consisted of one albumin molecule and two Fab' molecules was confirmed by N-terminal sequencing of unfractionated final product, also. This also showed that no Fab' light chain had dissociated during production and that the covalent linkage between Fab' and albumin was via the Fab' heavy chain, only.

Ligand binding activity was retained by the conjugate, as shown by FACS analysis of its binding to cells bearing ligand on their surface. Scatchard analysis of binding gave a 2-phase curve, with a $K_D$ of 8 nM for binding of one of the two Fab's, and 3 nM for binding of both Fab's in the construct (FIG. 9). These values were similar to those of a control (Fab' dimerised by crosslinking with bis-maleimido hexane i.e. lacking the albumin moiety), being 12 nM and 3 nM, respectively. As in the other two Examples, maintenance of the Fab's full binding activity despite the attachment of a large molecular weight moiety was probably due to the targeting of the Fab' hinge as the point of attachment, being at the opposite end of the molecule from the antigen binding function. In the present Example, the albumin interfered with neither Fab' to which it was attached.

Thus, this process produced a very specific, bivalent product. In contrast to Example 1, this was by modification of the immunoglobulin moiety, rather than the albumin, prior to the final stage of conjugation. Again in contrast to the other examples, a different immunoglobulin was used, exemplifying the general utility of the approach. Using such approaches, linkage of albumin to other polyspecific immunoglobulins would clearly generate polyspecific molecules with extended half-life in vivo.

The present results also exemplify inclusion of extra function in the conjugate. The present example is inclusion of a metal-chelating function, such as might be useful for assay, diagnosis or therapy. The chelating function in this example is on the linking moiety, and is a macrocycle that has previously been found to strongly bind metals, notably Indium, but possibly alternatively Copper, Gadolinium, Iron III, Cobalt III, Chromium III, Nickel or Aluminium.

Table 1.

Surface Plasmon Resonance Analysis of Binding of Ligand to Conjugate, Fusions and Other Immunoglobulins.

All immunoglobulins and derivatives were derived from the same anti-TNF antibody, and TNF was used as the ligand. See FIG. 10 for analysis of binding of RSA-F(ab')$_2$.

TABLE 1

Surface plasmon resonance analysis of binding of ligand to conjugate, fusions and other immunoglobulins

| | $k_a$, $10^5 M^{-1} s^{-1}$ | $k_d$, $10^{-4} s^{-1}$ | $K_D$, $10^{-10} M$ |
|---|---|---|---|
| IgG | 3.63 | 1.41 | 3.88 |
| Fab' | 2.79 | 0.56 | 2.01 |
| RSA- Fab' conjugate | 3.88 | 1.65 | 4.25 |
| scFv-HSA | 7.67 | 1.11 | 1.45 |
| scFv-G4S-HSA | 6.58 | 1.32 | 2.29 |
| scFv-UHL-HSA | 6.64 | 1.52 | 2.29 |
| scFv-$C_K$-HSA | 7.09 | 0.95 | 1.34 |

The invention claimed is:

1. A hybrid protein comprising one antigen-binding antibody fragment covalently linked to an albumin molecule, wherein the antibody fragment and albumin are indirectly linked by a bridging molecule of length from around 10 Å to around 20 Å between the thiol group of a cysteine residue present in the antibody fragment and the thiol group of the cysteine residue present in the albumin at position 34.

2. A hybrid protein according to claim 1 wherein the bridging molecule is an optionally substituted hexylene chain.

3. A hybrid protein according to claim 1 wherein the antibody fragment is a monovalent Fab fragment optionally containing one or more additional amino acids attached to the C-terminus of the CH1 domain.

4. A hybrid protein according to claim 2 wherein the antibody fragment is a monovalent Fab or Fab' fragment.

5. A hybrid protein according to claim 1 covalently linked to one or more effector or reporter groups.

6. A pharmaceutical composition comprising of a hybrid protein according to claim 1 together with one or more pharmaceutically acceptable excipients, diluents or carriers.

7. A hybrid protein consisting of one antigen-binding antibody fragment covalently linked to an albumin molecule, wherein the antibody fragment and albumin are indirectly linked by a bridging molecule of length from around 10 Å to around 20 Å between the thiol group of a cysteine residue present in the antibody fragment and the thiol group of the cysteine residue present in the albumin at position 34 wherein the antibody fragment and/or the bridging molecule are optionally linked to one or more effector or reporter groups.

8. A hybrid protein consisting of one antigen-binding antibody fragment covalently linked to an albumin molecule, wherein the antibody fragment and albumin are indirectly linked by a bridging molecule of length from around 10 Å to around 20 Å between the thiol group of a cysteine residue present in the antibody fragment and the thiol group of the cysteine residue present in the albumin at position 34.

* * * * *